US009833289B2

(12) United States Patent
Schuele et al.

(10) Patent No.: US 9,833,289 B2
(45) Date of Patent: Dec. 5, 2017

(54) METHOD AND APPARATUS FOR A RADIOLUCENT AND MRI COMPATIBLE CRANIAL STABILIZATION PIN

(71) Applicant: pro med instruments GmbH, Freiburg im Breisgau (DE)

(72) Inventors: Matthias E. Schuele, Freiburg (DE); Edgar F. Schuele, Freiburg (DE); Matt Mastromatteo, Sarasota, FL (US)

(73) Assignee: pro med instruments, GmbH, Freiburg im Breisgau (DE)

( * ) Notice: Subject to any disclaimer, the term of this patent is extended or adjusted under 35 U.S.C. 154(b) by 388 days.

(21) Appl. No.: 14/674,013

(22) Filed: Mar. 31, 2015

(65) Prior Publication Data

US 2015/0202012 A1    Jul. 23, 2015

Related U.S. Application Data

(63) Continuation-in-part of application No. 12/712,716, filed on Feb. 25, 2010, now Pat. No. 9,078,679.
(Continued)

(51) Int. Cl.
*A61B 17/04* (2006.01)
*A61B 17/84* (2006.01)
(Continued)

(52) U.S. Cl.
CPC .......... *A61B 19/203* (2013.01); *A61B 5/0555* (2013.01); *A61B 6/032* (2013.01);
(Continued)

(58) Field of Classification Search
CPC combination set(s) only.
See application file for complete search history.

(56) References Cited

U.S. PATENT DOCUMENTS 3,835,861 A    9/1974 Kees et al.
4,169,478 A    10/1979 Hickman
(Continued)

FOREIGN PATENT DOCUMENTS

EP    1 026 513    8/2000
EP    2 014 251    1/2009
(Continued)

OTHER PUBLICATIONS

Screenshots from www.integra-ls.com, printed Dec. 8, 2005.
(Continued)

*Primary Examiner* — Sameh Boles
(74) *Attorney, Agent, or Firm* — Frost Brown Todd LLC

(57) ABSTRACT

A substantially radiolucent cranial stabilization pin is adapted for use with a fixture for immobilizing a patient's head during a medical procedure. The pin includes a tip and a body, which are secured together to form the pin. The tip and body are constructed from non-ferrous, non-magnetic materials that are biocompatible. The tip and body are safe for use with, and compatible with, imaging techniques including MR imaging and CT imaging. In some examples the tip is a titanium insert and the body is molded within and around at least a portion of the tip. In some versions, the tip includes a hollow portion and one or more projections extending within the hollow portion. The molded body flows into the hollow portion and around the one or more projections of the tip creating a secure pin suitable to withstand torque and axial forces observed in use.

14 Claims, 31 Drawing Sheets

Related U.S. Application Data

(60) Provisional application No. 61/155,701, filed on Feb. 26, 2009.

(51) Int. Cl.

| | | |
|---|---|---|
| *A61B 17/88* | (2006.01) | |
| *A61F 2/08* | (2006.01) | |
| *A61B 19/00* | (2006.01) | |
| *A61B 5/055* | (2006.01) | |
| *A61B 6/03* | (2006.01) | |
| *A61B 6/04* | (2006.01) | |
| *A61B 90/14* | (2016.01) | |
| *A61B 17/00* | (2006.01) | |

(52) U.S. Cl.
CPC ................ *A61B 6/04* (2013.01); *A61B 90/14* (2016.02); *A61B 2017/0092* (2013.01); *A61B 2017/00911* (2013.01); *A61B 2017/00915* (2013.01)

(56) References Cited

U.S. PATENT DOCUMENTS

| | | |
|---|---|---|
| 4,392,645 A | 7/1983 | Westphal |
| 4,397,307 A | 8/1983 | Keller |
| 4,444,179 A | 4/1984 | Trippi |
| 4,475,550 A | 10/1984 | Bremer et al. |
| 4,539,979 A | 9/1985 | Bremer |
| 4,541,421 A | 9/1985 | Iversen et al. |
| 4,612,930 A | 9/1986 | Bremer |
| 4,796,846 A | 1/1989 | Meier et al. |
| 4,838,264 A | 6/1989 | Bremer et al. |
| 5,042,462 A | 8/1991 | Bremer |
| 5,062,415 A | 11/1991 | Weatherby et al. |
| 5,122,132 A | 6/1992 | Bremer |
| 5,156,588 A | 10/1992 | Marcune et al. |
| 5,180,361 A | 1/1993 | Moore et al. |
| 5,197,965 A | 3/1993 | Cherry et al. |
| 5,254,079 A | 10/1993 | Agbodoe et al. |
| 5,276,927 A | 1/1994 | Day |
| 5,300,076 A | 4/1994 | Leriche |
| 5,302,170 A | 4/1994 | Tweardy |
| 5,318,509 A | 6/1994 | Agbodoe |
| 5,347,894 A | 9/1994 | Fischer |
| 5,437,612 A | 8/1995 | Moore et al. |
| 5,537,704 A | 7/1996 | Dinkler et al. |
| 5,549,620 A | 8/1996 | Bremer |
| 5,632,722 A | 5/1997 | Tweardy et al. |
| 5,643,268 A | 7/1997 | Vilsmeier et al. |
| 5,961,528 A | 10/1999 | Birk et al. |
| 6,045,553 A | 4/2000 | Iversen et al. |
| 6,306,146 B1 | 10/2001 | Dinkler |
| 6,379,362 B1 | 4/2002 | Birk et al. |
| 6,598,275 B1 | 7/2003 | Kolody et al. |
| 6,635,064 B2 | 10/2003 | U et al. |
| 6,684,428 B2 | 2/2004 | Grotenhuis et al. |
| 6,896,678 B2 | 5/2005 | Tweardy |
| 7,011,619 B1 | 3/2006 | Lewis et al. |
| 7,048,735 B2 | 5/2006 | Ferrante et al. |
| 7,246,975 B2 | 7/2007 | Corso et al. |
| 7,507,244 B2 | 3/2009 | Dinkler |
| 7,836,532 B2 | 11/2010 | Schüle |
| 7,905,884 B2 | 3/2011 | Simonton et al. |
| 8,104,477 B2 | 1/2012 | Edlauer et al. |
| 8,623,029 B2 | 1/2014 | Bailey et al. |
| 8,939,976 B2 | 1/2015 | Dinkler |
| 9,078,679 B2 | 7/2015 | Schuele et al. |
| 9,402,692 B2 | 8/2016 | Schuele |
| 2007/0270801 A1 | 11/2007 | Arn et al. |
| 2010/0059064 A1 | 3/2010 | Schüle et al. |
| 2011/0257689 A1* | 10/2011 | Fiechter ............ A61B 17/8685 606/301 |

FOREIGN PATENT DOCUMENTS

| | | |
|---|---|---|
| WO | WO 97/40764 | 4/1997 |
| WO | WO 02/085187 | 10/2002 |

OTHER PUBLICATIONS

Screenshots from www.integra-ls.com, printed Jan. 28, 2005.
Screenshots of Surgical Tables Accessories from www.bicakcilar.com, printed Jan. 28, 2005.
EPO Search Report dated May 11, 2006 for Application No. EP 05292169.
International Search Report dated Oct. 18, 2010 for Application No. PCT/IB2010/000513.
International Preliminary Report on Patentability dated Aug. 30, 2011 for Application No. PCT/IB2010/000513.
Notification Concerning Transmittal of International Preliminary Report on Patentability (Chapter 1 of the Patent Cooperation Treaty) dated Sep. 9, 2011 for Application No. PCT/IB2010/000513.

* cited by examiner ns and components include any 35 of the DORO products of pro med instruments GmbH of

METHOD AND APPARATUS FOR A RADIOLUCENT AND MRI COMPATIBLE CRANIAL STABILIZATION PIN

PRIORITY

This application is a continuation-in-part of U.S. Non-Provisional patent application Ser. No. 12/712,716, filed Feb. 25, 2010, entitled "METHOD AND APPARATUS FOR A RADIOLUCENT AND MRI COMPATIBLE CRANIAL STABLIZATION PIN," the disclosure of which is incorporated by reference herein, which was a Non-Provisional of U.S. Provisional Patent Application Ser. No. 61/155,701, entitled "METHOD AND APPARATUS FOR A RADIOLUCENT CRANIAL STABILIZATION PIN," filed Feb. 26, 2009, the disclosure of which is incorporated by reference herein.

BACKGROUND

During some surgical operations or other procedures, a portion of the body upon which surgery is being conducted may be substantially immobilized, such as, for example, a patient's head during head or neck surgery. Such immobilization of a patient's head, for example, may be accomplished with a fixture such as a skull clamp or other fixture, as disclosed in U.S. Pat. No. 7,836,532, entitled METHOD AND APPARATUS FOR ATTACHING ACCESSORIES TO A SURGICAL FIXTURE, issued Nov. 23, 2010, and in U.S. Patent Publication No. 2010/0059064, METHOD AND APPARATUS FOR USING A SURGICAL FIXTURE IN AN INTRA-OPERATIVE COMPUTED TOMOGRAPHY SCANNER, published Mar. 11, 2010, the disclosures of which are incorporated by reference herein. Other examples of cranial stabilization systems and components include any of the DORO products of pro med instruments GmbH of Freiburg, Germany. These and other devices may be used with cranial stabilization pins, also referred to as skull pins, which may be used to securely hold a patient's head within the skull clamp or other device.

It may be desirable to use such a cranial immobilization system or technique with a surgical procedure using intra-operative computed tomography (CT) scanning or other types of imaging (e.g., MRI, PEM, X-Ray, etc.). In some circumstances, it may be desirable and convenient for components of the cranial immobilization system to be compatible with the imaging technology, e.g. MRI, and further radiolucent. For example, it may be desirable that the skull pins be substantially or completely radiolucent and safe for use with MRI, yet still provide sufficient durability in use. While many surgical accessories and immobilization fixtures exist, it is believed that no one prior to the inventors has created or used the invention described herein.

BRIEF DESCRIPTION OF THE DRAWINGS

The accompanying drawings incorporated in and forming a part of the specification illustrate several aspects of the present invention, and together with the description serve to explain the principles of the invention; it being understood, however, that this invention is not limited to the precise arrangements shown. In the drawings, like reference numerals refer to like elements in the several views. In the drawings.

DETAILED DESCRIPTION

Figure 1:
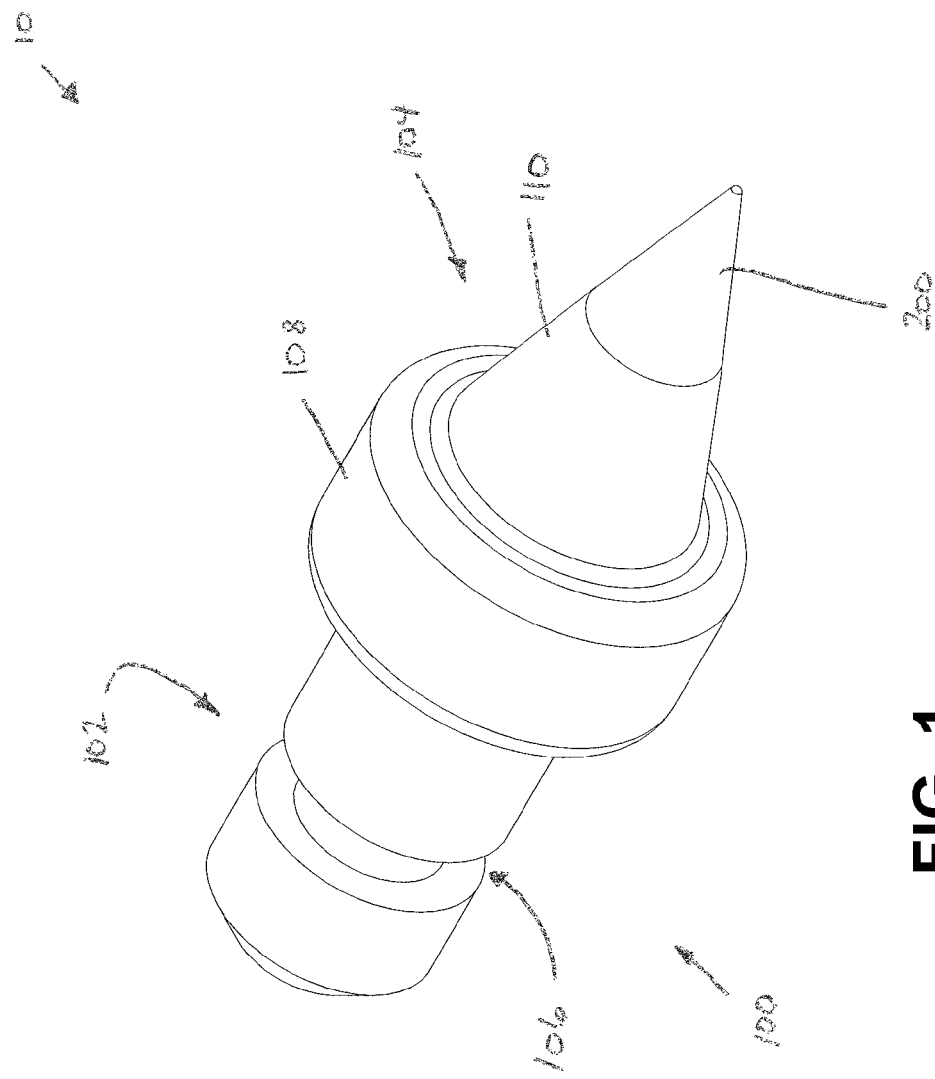
FIG. 1 depicts a perspective view of an exemplary cranial stabilization pin.

The following description of certain examples of the invention should not be used to limit the scope of the present invention. Other examples, features, aspects, versions, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the descriptions should be regarded as illustrative in nature and not restrictive.

FIGS. 1-31 depict various views of exemplary cranial stabilization pins, or components thereof, configured for use in a cranial immobilization fixture as referenced and described above. Such cranial stabilization pins are sometimes referred to as skull pins, or pins. The pins are configured to be safe for use with and compatible with imaging techniques including x-ray, computed tomography (CT) and magnetic resonance (MR). The pins are at least partially radiolucent and are configured to produce only a minimal artifact in the output of an imaging scan. The pins are constructed such that they can withstand the torque and axial forces typical in a skull stabilization procedure.

Referring to FIGS. 1-6, an exemplary version of cranial stabilization pin (10) is shown. Pin (10) comprises a body (100) and tip (200). Body (100) comprises proximal end (102) and distal end (104). Proximal end (102) is configured for secure attachment with a pin-holding component of a skull clamp or other device, e.g. a skull clamp as described in U.S. Pat. No. 7,836,532, entitled METHOD AND APPARATUS FOR ATTACHING ACCESSORIES TO A SURGICAL FIXTURE, issued Nov. 23, 2010, or in U.S. Patent Publication No. 2010/0059064, METHOD AND APPARATUS FOR USING A SURGICAL FIXTURE IN AN INTRA-OPERATIVE COMPUTED TOMOGRAPHY SCANNER, published Mar. 11, 2010, the disclosures of which are incorporated by reference herein. By way of example, proximal end (102) has a generally cylindrical shape that is configured to fit within a matching bore of a pin-holding component of a skull clamp. In the example shown in FIG. 1, proximal end (102) includes an annular recess (106). Annular recess (106) allows for a pin-holding component of a skull clamp to grip proximal end (102) of pin (10). Annular recess (106) may also be fitted with an o-ring (not shown) to assist in securing to the pin-holding component of a skull clamp or other device. In some other versions, proximal end (102) lacks annular recess (106). Other suitable features and configurations that may be provided at proximal end (102) such that pin (10) can be associated with a pin-holding component of a skull clamp or other device will be apparent to those of ordinary skill in the art in view of the teachings herein.

Distal end (104) of pin (10) of the present example comprises annular collar (108) and a conical protrusion (110). Annular collar (108) provides first surface (112) that is configured to act as a stop by contacting a portion of a pin-holding component of a skull clamp or other device. Conical protrusion (110) extends distally from body (100), tapering from larger to smaller diameter as protrusion (110) extends distally. At a distal-most end, conical protrusion (110) is associated with tip (200). Of course, distal end (104) of pin (10) may have a variety of other types of features and configurations in addition to or in lieu of having annular collar (108) and/or conical protrusion (110).

Figure 4:
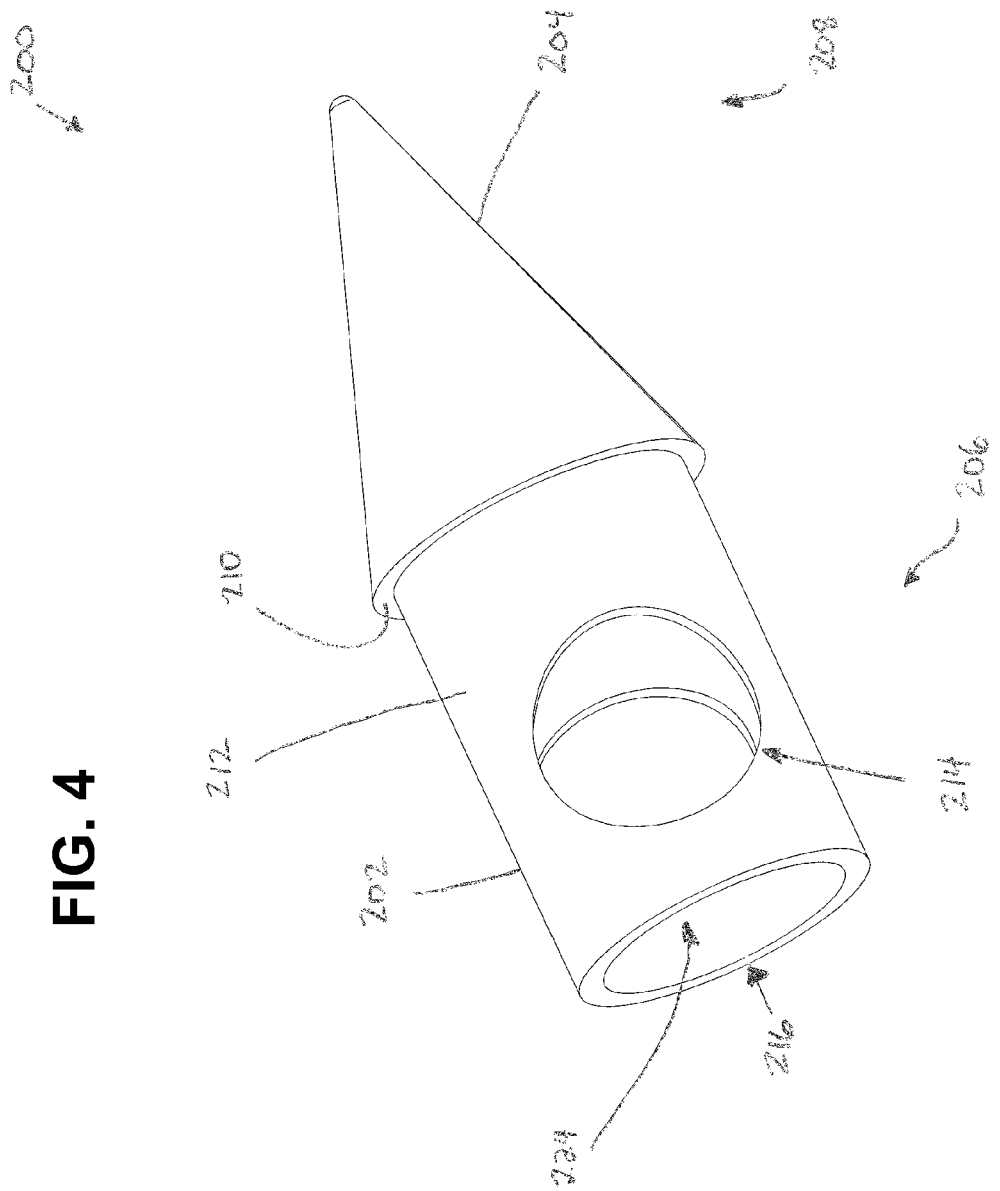
FIG. 4 depicts a perspective view of the tip of the pin of FIG. 1.

Tip (200) is largely a hollow structure comprising shaft (202) and conical protrusion (204). Shaft (202) is located along proximal end (206) of tip (200), and conical protrusion (204) is located along distal end (208) of tip (200). Conical protrusion (204) extends distally from shaft (202), tapering to a point at its distal-most end. At its proximal-most end, conical protrusion (204) includes lip (210). Lip (210) has a diameter greater than shaft (202) such that lip (210) overhangs shaft (202). Shaft (202) comprises sidewall (212), and sidewall (212) is configured with one or more openings (214). For example, as shown in FIG. 4, sidewall (212) includes two circular-shaped openings (214). Shaft (202) also comprises open end (216), which provides access to void space (224) within tip (200).

Figure 5:
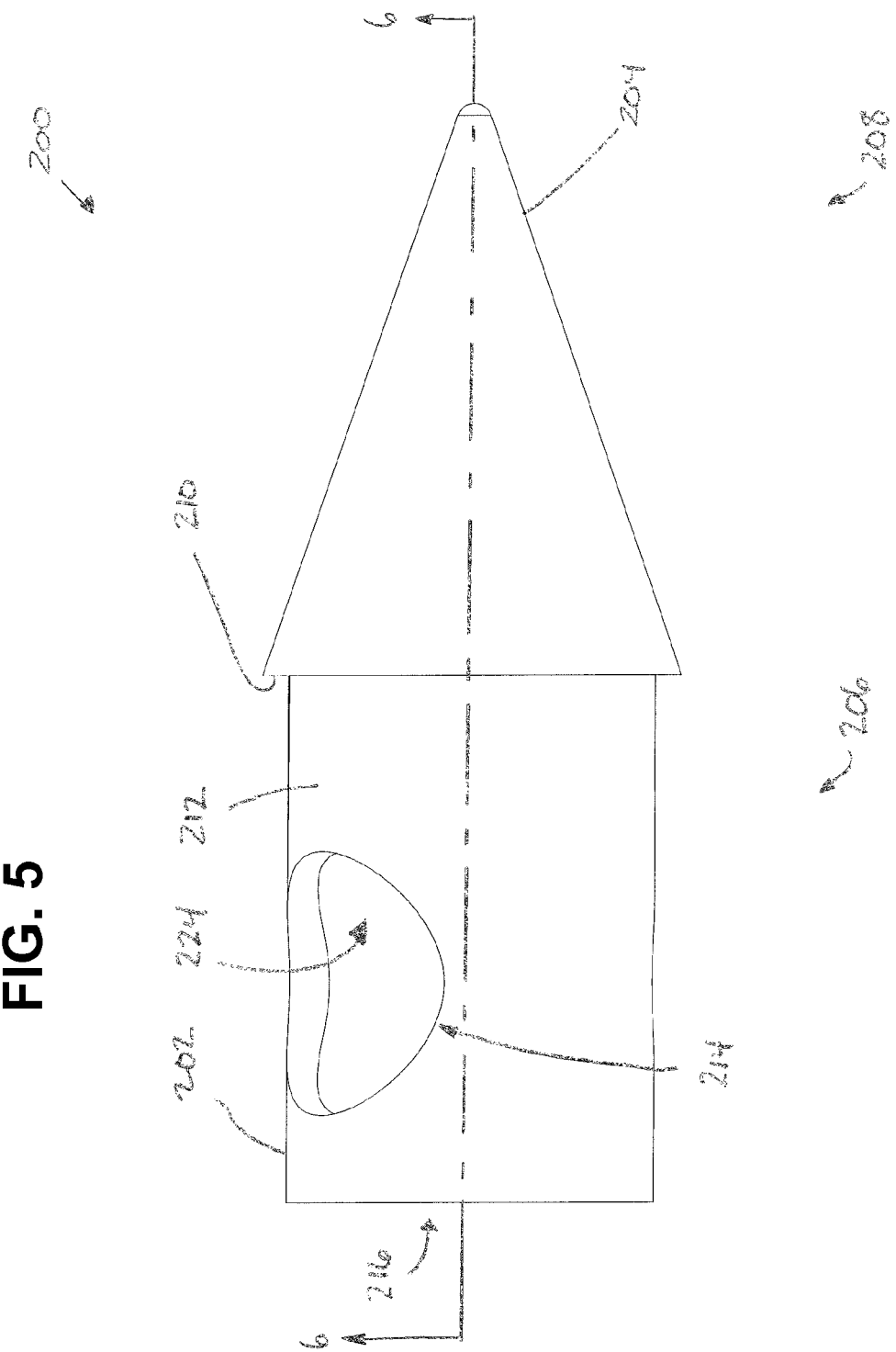
FIG. 5 depicts a side view of the tip of FIG. 4.

In some versions, tip (200) is constructed from a non-magnetic metal, such as titanium. During fabrication, a solid piece of titanium is milled and/or turned to create the general shape as shown in FIGS. 4 and 5. After milling and/or turning, the shaped titanium piece is drilled to incorporate openings (214) in sidewall (212). An additional drilling act is then used to hollow-out tip (200) by drilling along the longitudinal axis of tip (200) to create open end (216) and void space (224). Based on the teachings herein, other ways to fabricate tip (200) and other materials suitable for tip (200) will be apparent to those of ordinary skill in the art. By way of example only, other suitable materials to fabric the tips disclosed herein may include ceramics, other non-magnetic metals, glass-fiber reinforced materials, carbon-fiber reinforced materials, among others.

Figure 2:
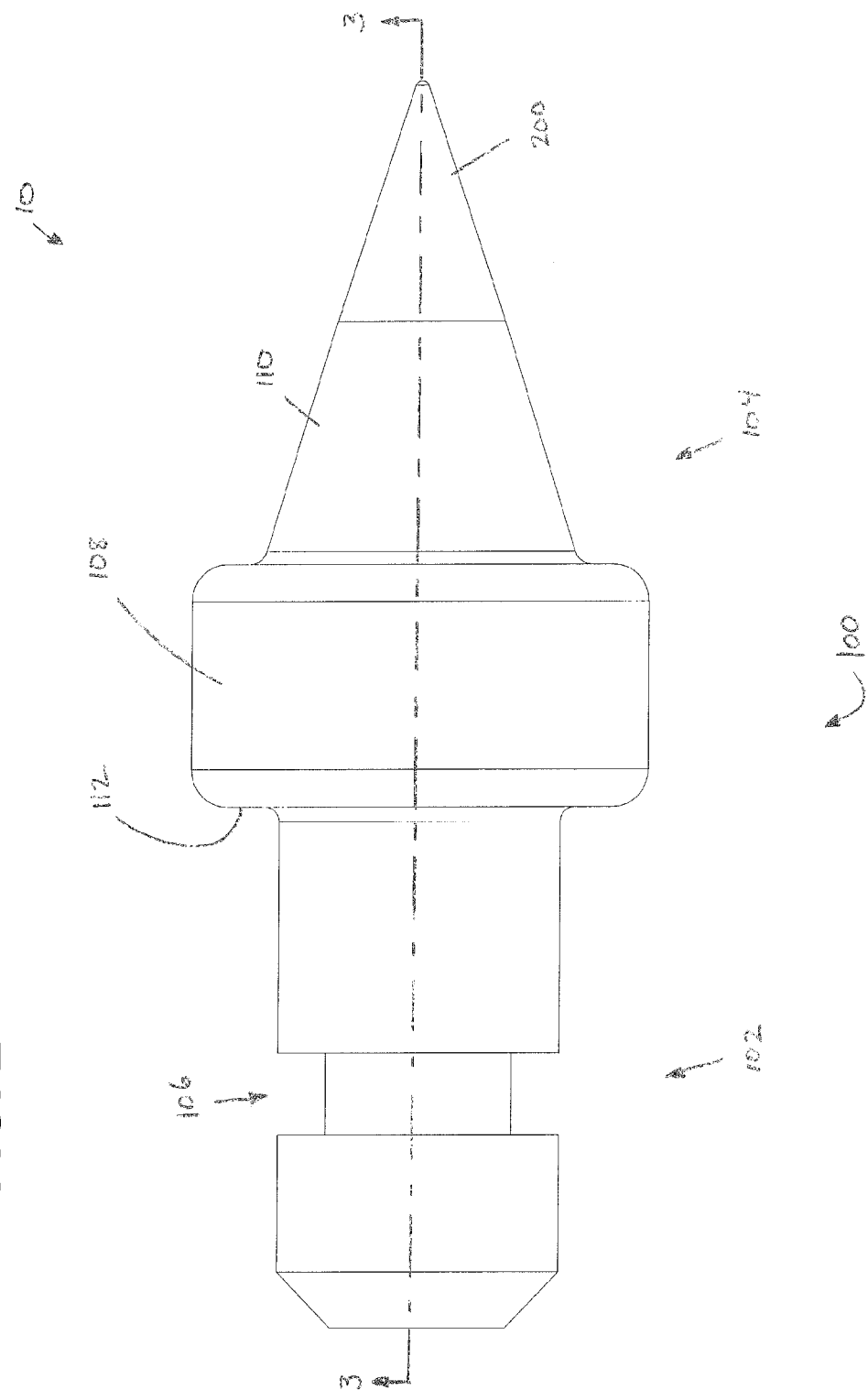
FIG. 2 depicts a side view of the pin of FIG. 1.

In some versions, body (100) is constructed from a plastic by an injection molding process. Suitable plastics may include polyether-etherketone (PEEK), duroplastic, and/or other thermoplastics or thermosetting plastics, all or any of which may include glass-fiber and/or carbon-fiber reinforcement. Moreover, in some versions, body (100) and tip (200) are securely joined via the injection molding process. For example, tip (200) is positioned within the injection mold as an insert, and body (100) is molded around and within tip (200). Where such a process is used, the molten plastic flows into void space (224) of tip (200) via open end (216) of shaft (202) and openings (214) in sidewall (212). The molten plastic fills void space (224) within tip (200) and overflows to encapsulate shaft (202). The shape of the mold is such that the molten plastic continues to form body (100) in the shape as shown in FIGS. 1-2.

Figure 3:
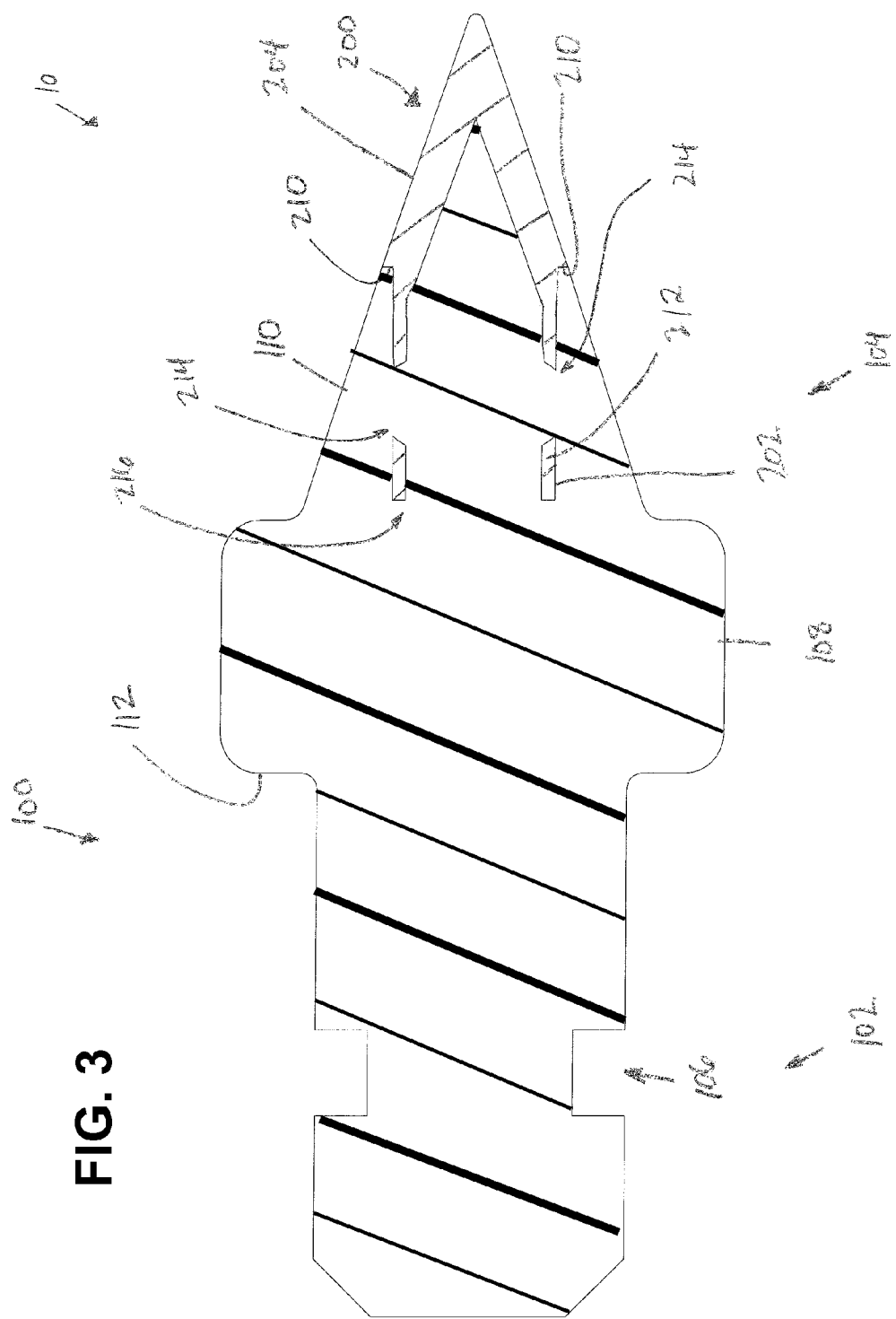
FIG. 3 depicts a cross section view of the pin of FIG. 2, taken along line 3-3 of FIG. 2.
Figure 6:
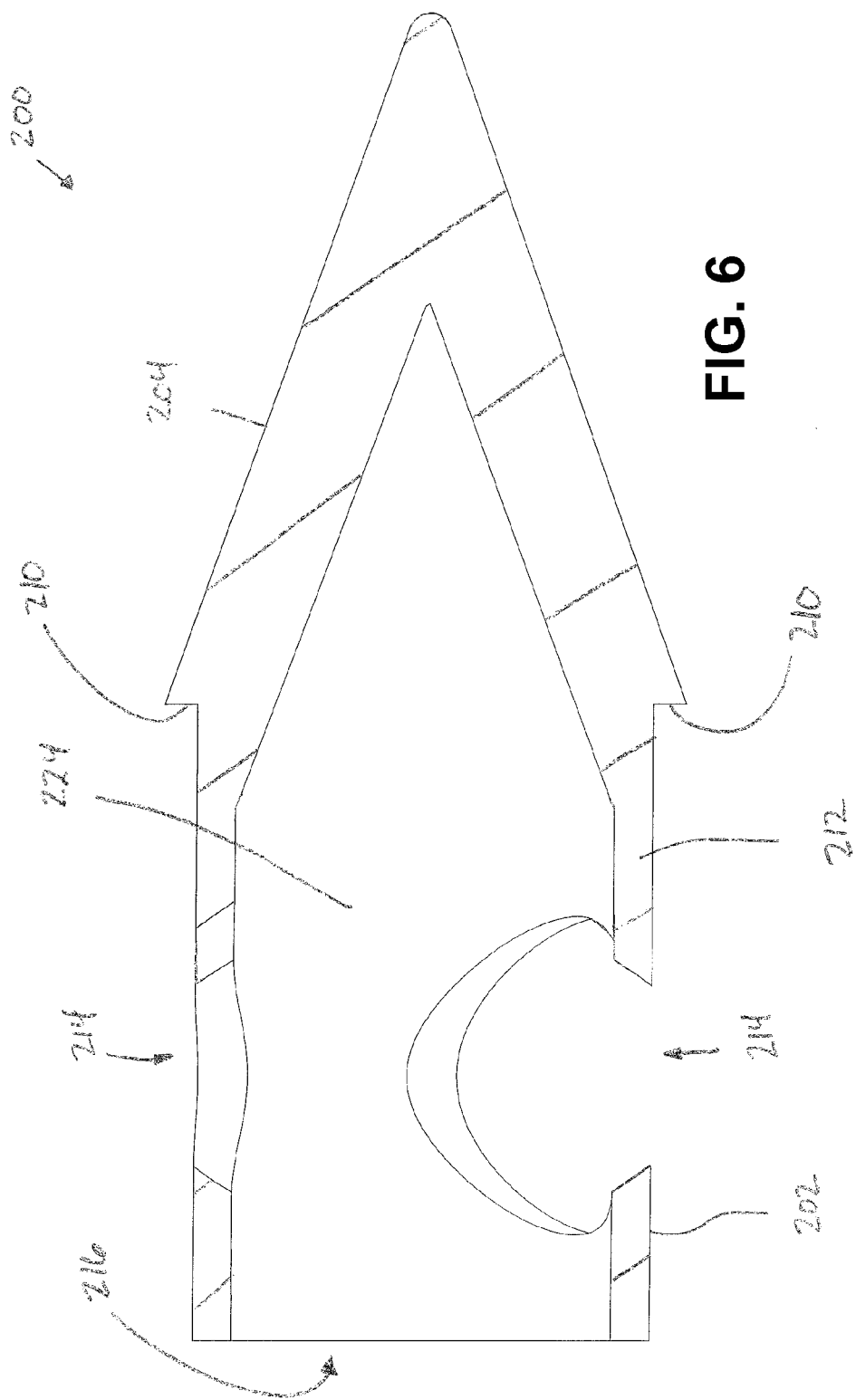
FIG. 6 depicts a cross section view of the tip of FIG. 5, taken along the line 6-6 of FIG. 5.

Referring to FIGS. 3 and 6, cross sections of pin (10) and tip (200) show that final pin (10), in an injection molded design, has the plastic of body (100) encompassing void space (224) of tip (200) and surrounding proximal end (206) of tip (200) where shaft (202) is located. Also, lip (210) of tip (200) abuts conical protrusion (110) of body (100) to provide a smooth transition from tip (200) to body (100). Using such a design and fabrication process, pin (10) is safe for use with and compatible with MR imaging, and pin (10) is substantially radiolucent with a strong tip (200) having low mass such that only a minimal artifact is seen in the output of an imaging scan. Furthermore, using such a design and fabrication process, tip (200) and body (100) are securely joined such that pin (10) can withstand the torque and axial forces typical in a skull stabilization procedure using a skull clamp or other device. For instance, molding body (100) to tip (200) by molding plastic not only around the exterior surface of a portion of a low mass tip (200), but also within and through portions of tip (200) provides as strong and secure connection between body (100) and tip (200), suitable for withstanding torque and axial forces experienced in use.

While body (100) has been described as being constructed of plastic, and by an injection molding process, other suitable materials and methods of construction will be apparent to those of ordinary skill in the art in view the teachings herein. For example, body (100) may be fabricated by machining by turning, milling, etc. instead of injection molding. Additionally, based on the teachings herein, other ways to securely join tip (200) and body (100) will be apparent to those of ordinary skill in the art. For example, tip (200) and body (100) may be securely joined with an adhesive.

Referring to FIGS. 7-10, another exemplary pin (20) is shown. Pin (20) generally has the same or similar appearance as pin (10), as shown in FIGS. 1-2. In fact, pin (20) is identical to pin (10) with the exception that pin (20) comprises a different tip. Thus the functionality of pin (20) is the same or similar to pin (10) and the preceding paragraphs describing the functionality of pin (10) apply equally to pin (20).

Pin (20) comprises body (300) and tip (400). Tip (400) is largely a hollow structure comprising shaft (402), conical protrusion (404), and collar (405). Collar (405) is located along proximal end (406) of tip (400), and conical protrusion (404) is located along distal end (408) of tip (400). Shaft (402) extends between collar (405) and conical protrusion (404). Conical protrusion (404) extends distally from shaft (402), tapering to a point at its distal-most end. At its proximal-most end, conical protrusion (404) includes lip (410). Lip (410) has a diameter greater than shaft (402) such that lip (410) overhangs shaft (402). As shown in FIGS. 7-10, shaft (402) comprises sidewall (412) that is without openings as described above with respect to pin (10). Of course, in some versions openings similar to that shown with pin (10) may be incorporated into sidewall (412) of shaft (402). Shaft (402) extends proximally from lip (410) of conical protrusion (404) and terminates with its connection to collar (405). In the present example, collar (405) comprises a general u-shape, having circular flange portion (418) with first and second fins (420, 422) extending proximally from flange portion (418). Collar (405) also comprises open end (416) in the center of flange portion (418), which provides access to void space (424) within tip (400). Of course, in some versions collar (405) may have shapes other than a u-shape, e.g. a circular shape the same as or similar to that shown in FIG. 24.

Figure 8:
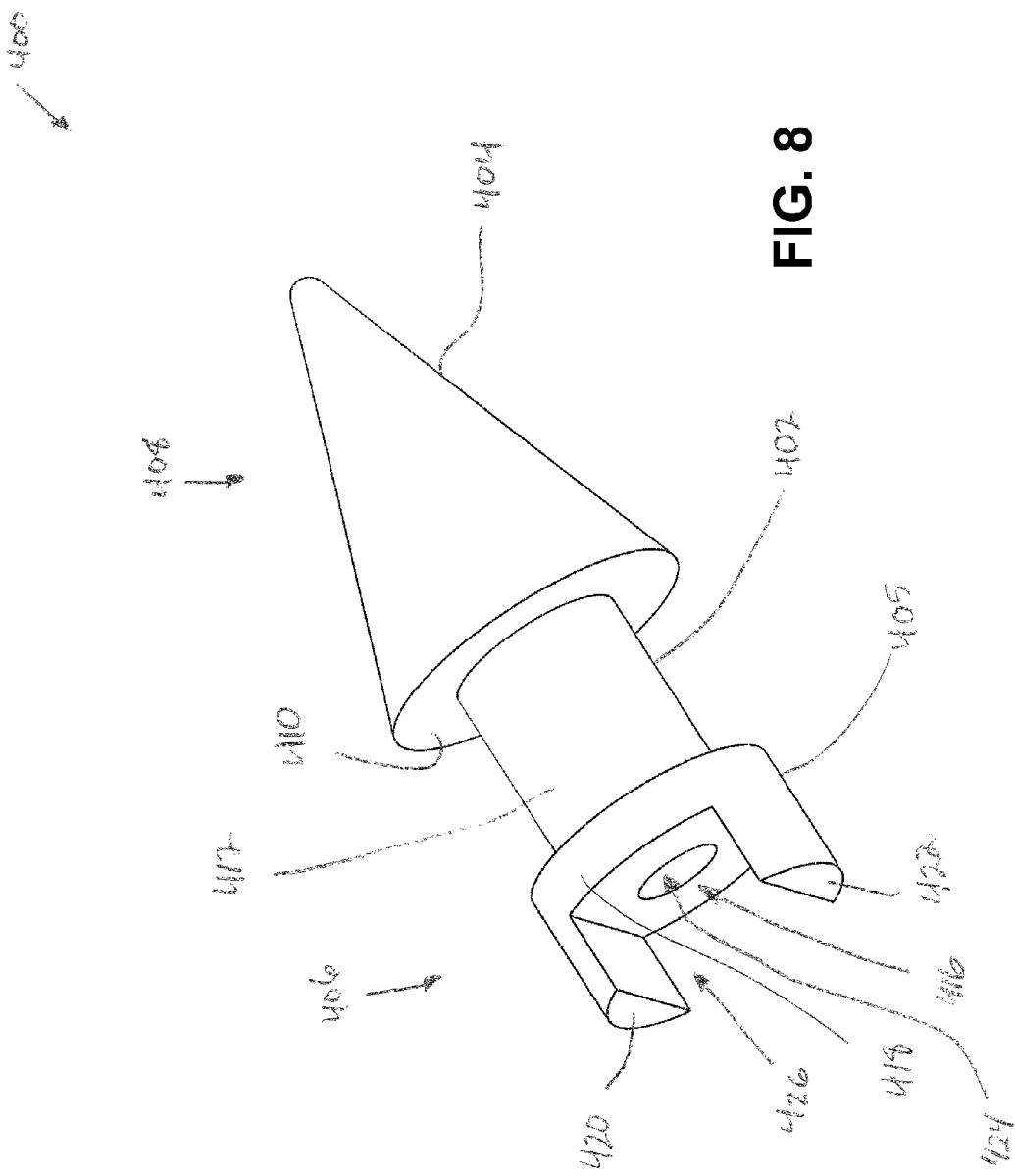
FIG. 8 depicts a perspective view of the tip of the pin of FIG. 7.
Figure 9:
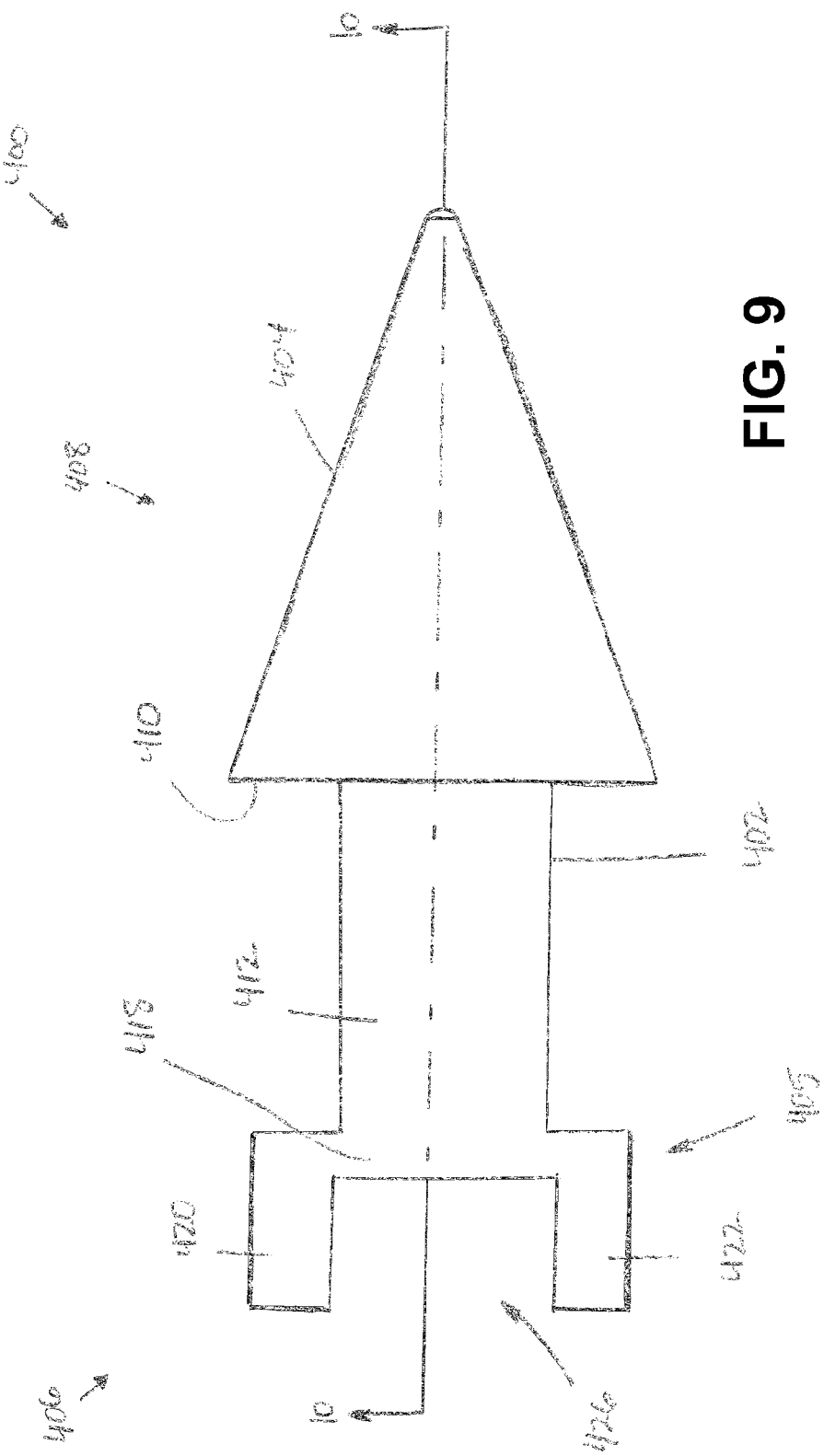
FIG. 9 depicts a side view of the tip of FIG. 8.

In some versions, tip (400) is constructed from a non-magnetic metal, such as titanium. During fabrication, a solid piece of titanium is milled and/or turned to create the general shape as shown in FIGS. 8 and 9. After milling and/or turning, the shaped titanium piece is drilled to hollow-out tip (400) by drilling along the longitudinal axis of tip (400). For example, drilling creates open end (416) of collar (405) and void space (424) extending from open end (416) through flange portion (418), through shaft (402), and into conical protrusion (404). Based on the teachings herein, other ways to fabricate tip (400) and other materials suitable for tip (400) will be apparent to those of ordinary skill in the art.

In some versions, body (300) is constructed from a plastic by an injection molding process. Suitable plastics may include polyether-etherketone (PEEK), duroplastic, and/or other thermoplastics or thermosetting plastics, all or any of which may include glass-fiber and/or carbon-fiber reinforcement. Moreover, in some versions, body (300) and tip (400) are securely joined via the injection molding process. For example, tip (400) is positioned within the injection mold as an insert, and body (300) is molded around and within tip (400). Where such a process is used, the molten plastic flows into void space (424) of tip (400) via open end (416) of collar (405). The molten plastic fills void space (424) within tip (400) and also surrounds shaft (402) and collar (405). The molten plastic further fills the space (426) of collar (405) between fins (420, 422). The shape of the mold is such that the molten plastic continues to form body (300) in the shape as shown in FIGS. 1-2.

Figure 7:
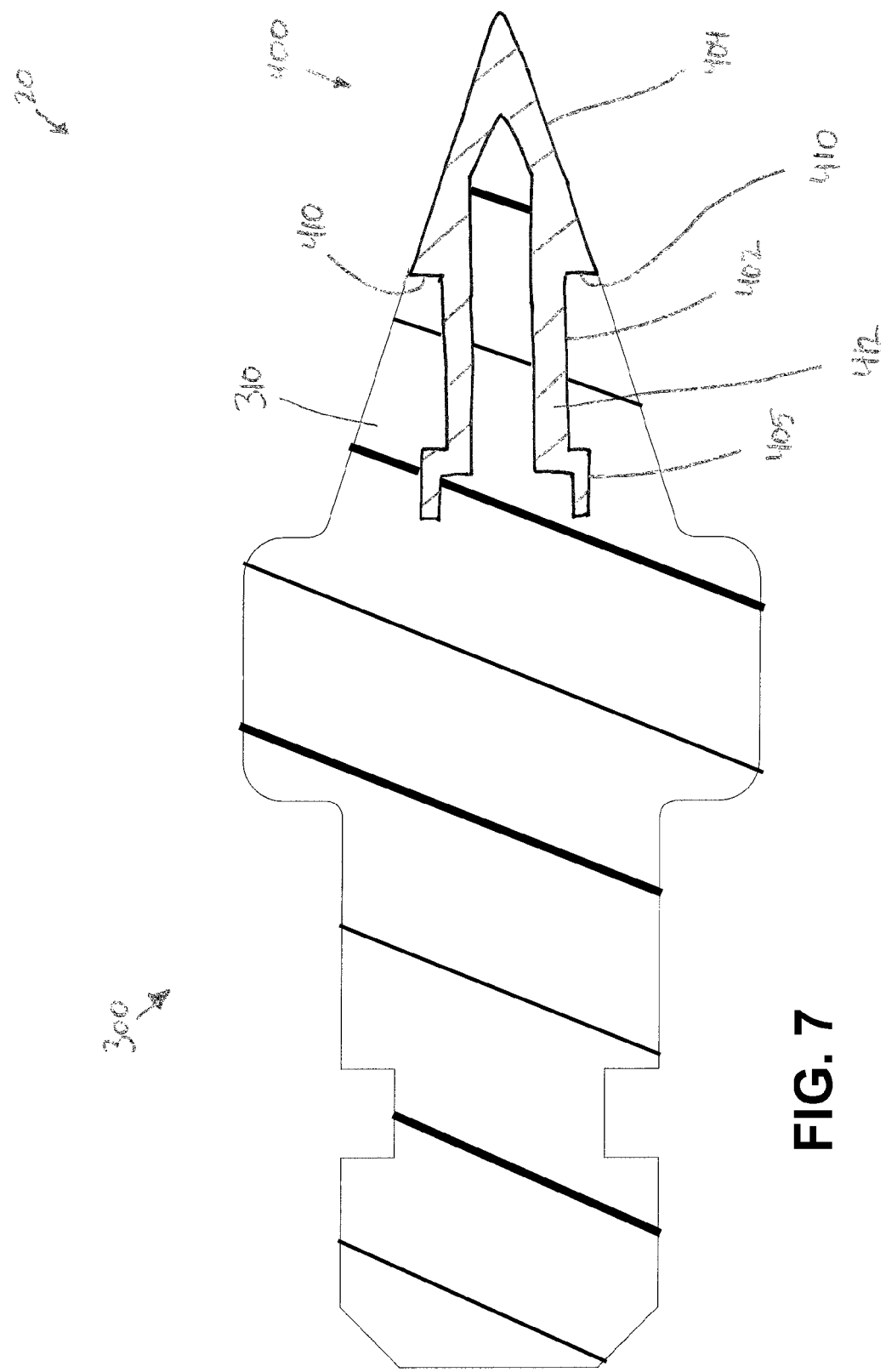
FIG. 7 depicts a cross section view of another exemplary cranial stabilization pin, taken along a line similar to that of the cross section view of FIG. 3 but for another exemplary pin that is not shown in perspective and side views but would otherwise be identical to the perspective and side views of FIGS. 1 and 2.
Figure 10:
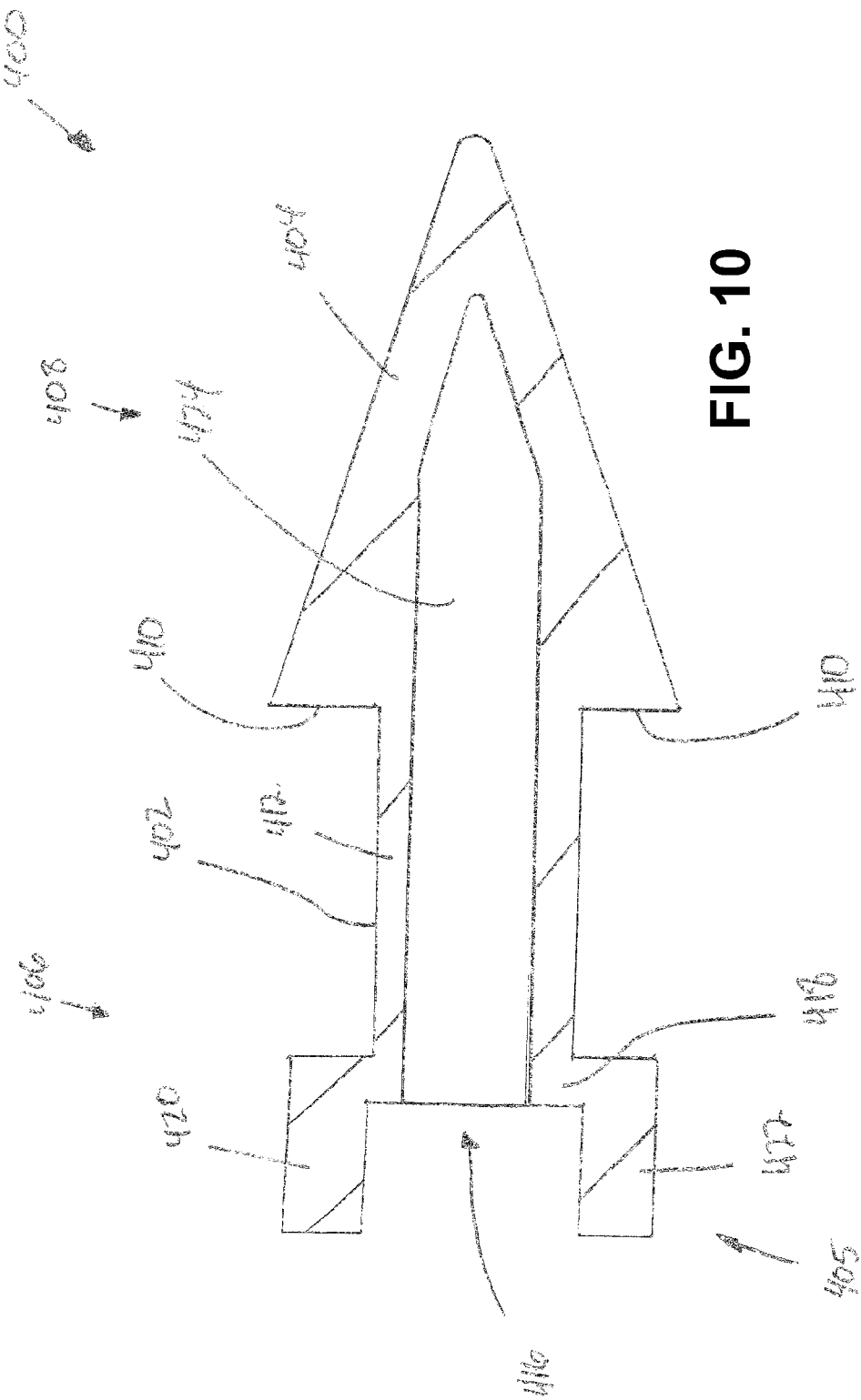
FIG. 10 depicts a cross section view of the tip of FIG. 9, taken along line 10-10 of FIG. 9.

Referring to FIGS. 7 and 10, cross sections of pin (20) and tip (400) show that final pin (20), in a molded design, has the plastic of body (100) encompassing void space (424) of tip (400) and surrounding shaft (402) and collar (405) of tip (400). Also, lip (410) of tip (400) abuts conical protrusion (310) of body (300) to provide a smooth transition from tip (400) to body (300). Using such a design and fabrication process, pin (20) is safe for use with and compatible with MR imaging, and is substantially radiolucent with a strong tip (400) having low mass such that only a minimal artifact is seen in the output of an imaging scan. Furthermore, using such a design and fabrication process, tip (400) and body (300) are securely joined such that pin (20) can withstand the torque and axial forces typical in a skull stabilization procedure using a skull clamp or other device. For instance, molding body (300) to tip (400) by molding plastic not only around the exterior surface of a portion of a low mass tip (400), but also within and through portions of tip (400) provides as strong and secure connection between body (300) and tip (400), suitable for withstanding torque and axial forces experienced in use.

While body (300) has been described as being constructed of plastic, and by an injection molding process, other suitable materials of construction and processes by which to construct body (300) will be apparent to those of ordinary skill in the art in view of the teachings herein. For example, body (300) may be fabricated by machining by turning, milling, etc. instead of injection molding. Additionally, other ways to securely join tip (400) and body (300) will be apparent to those of ordinary skill in the art in view of the teachings herein. For example, tip (400) and body (300) may be securely joined with an adhesive.

Figure 12:
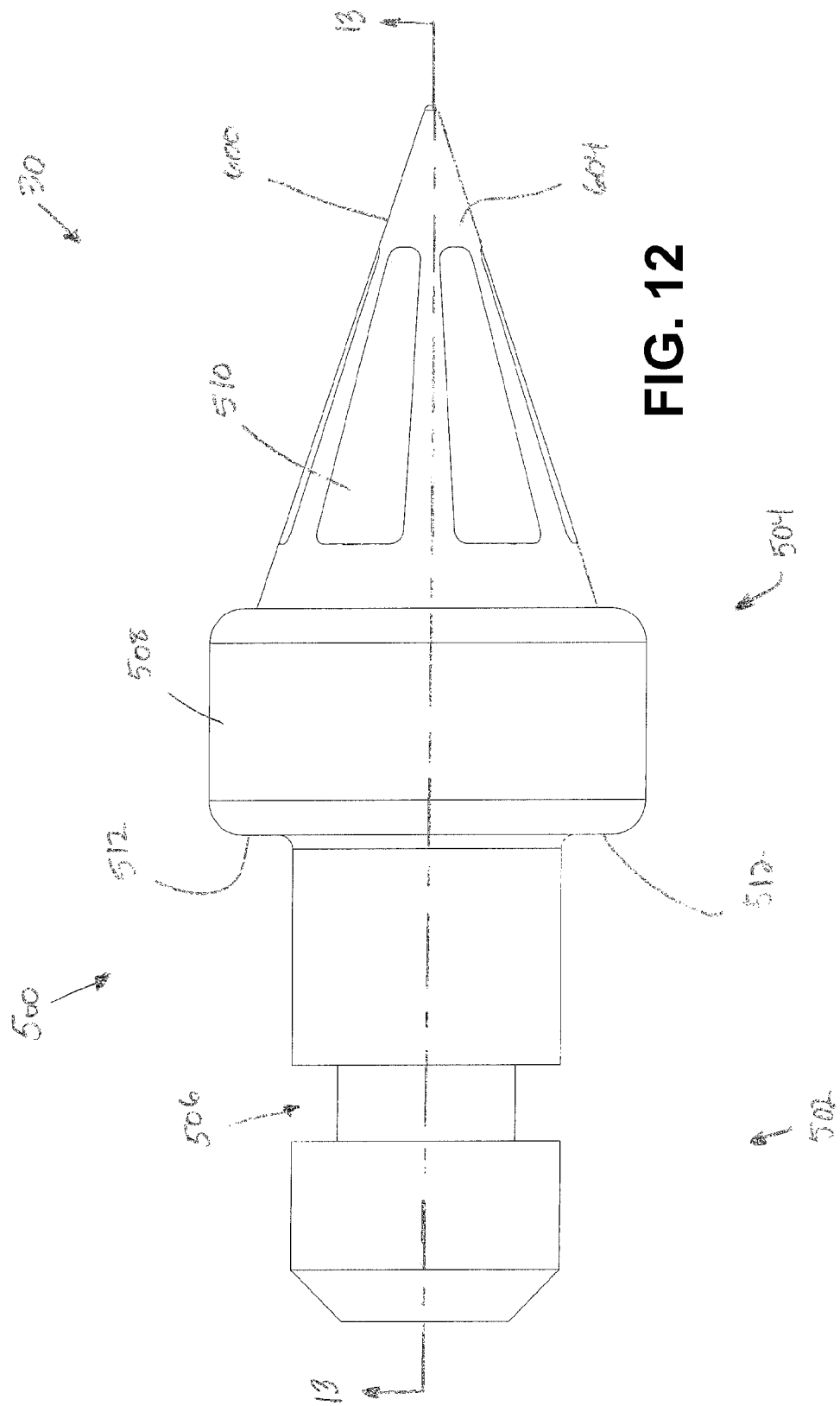
FIG. 12 depicts a side view of the pin of FIG. 11.
Figure 13:
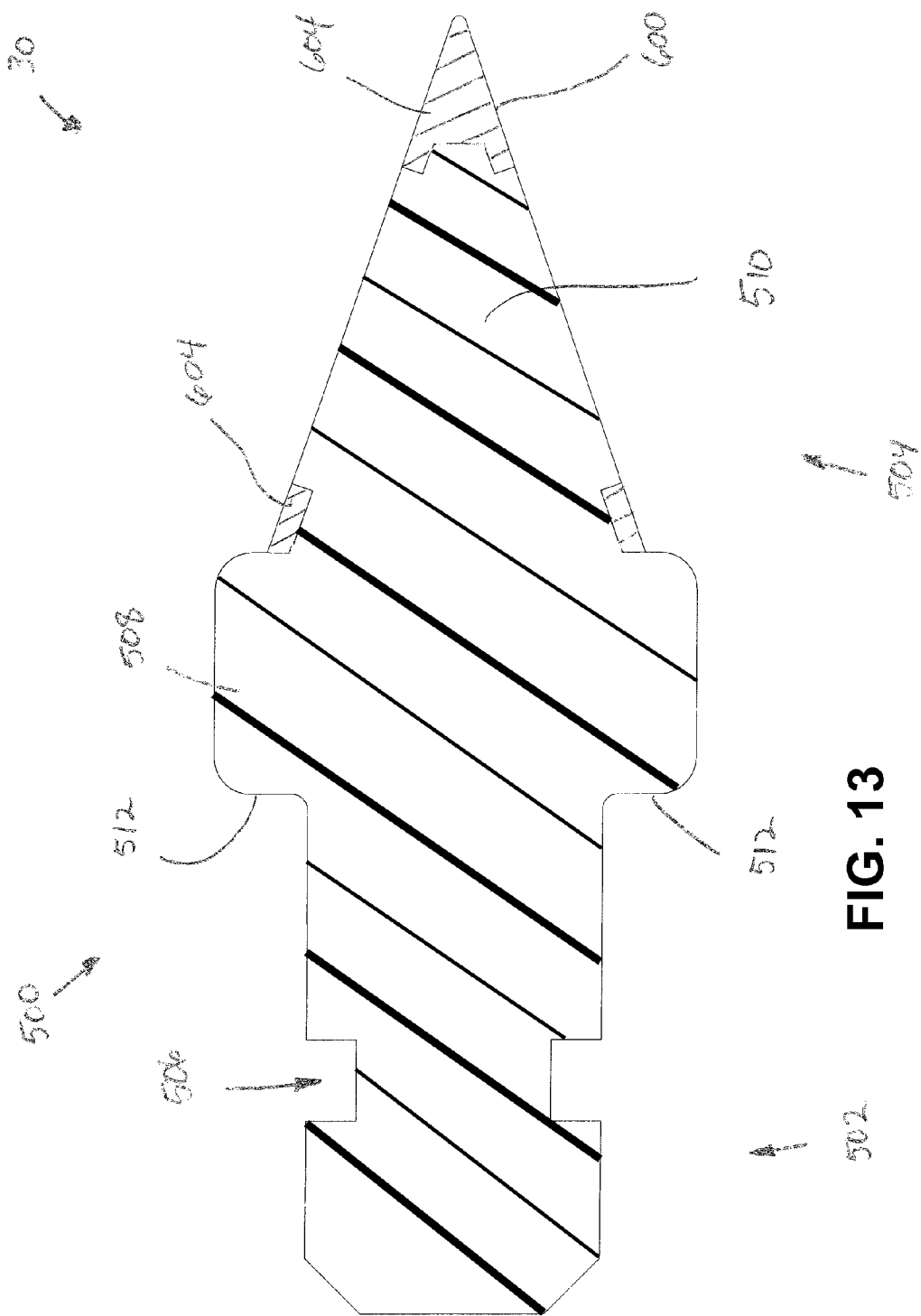
FIG. 13 depicts a cross section view of the pin of FIG. 12, taken along line 13-13 of FIG. 12.
Figure 14:
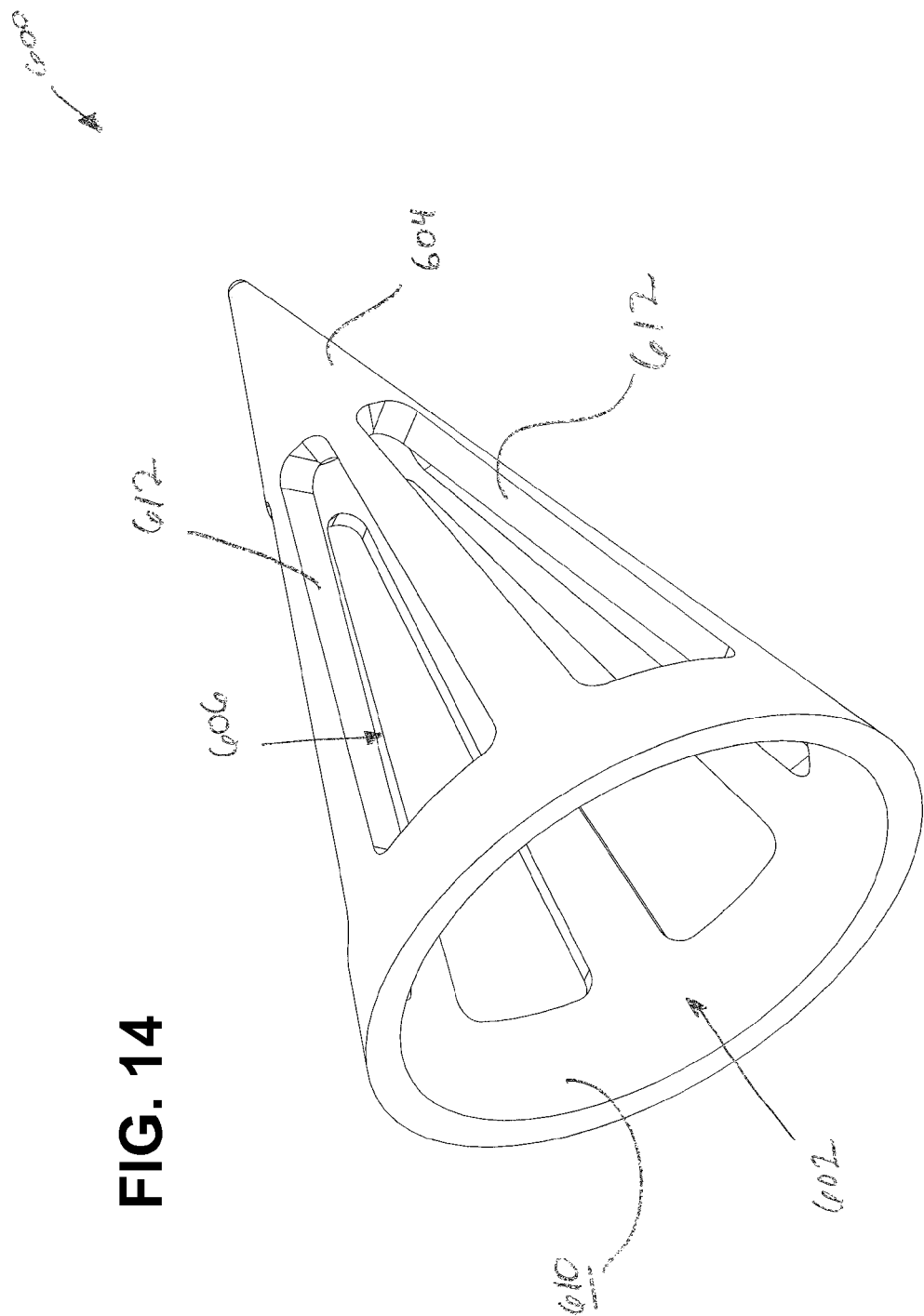
FIG. 14 depicts a perspective view of the tip of the pin of FIG. 11.
Figure 15:
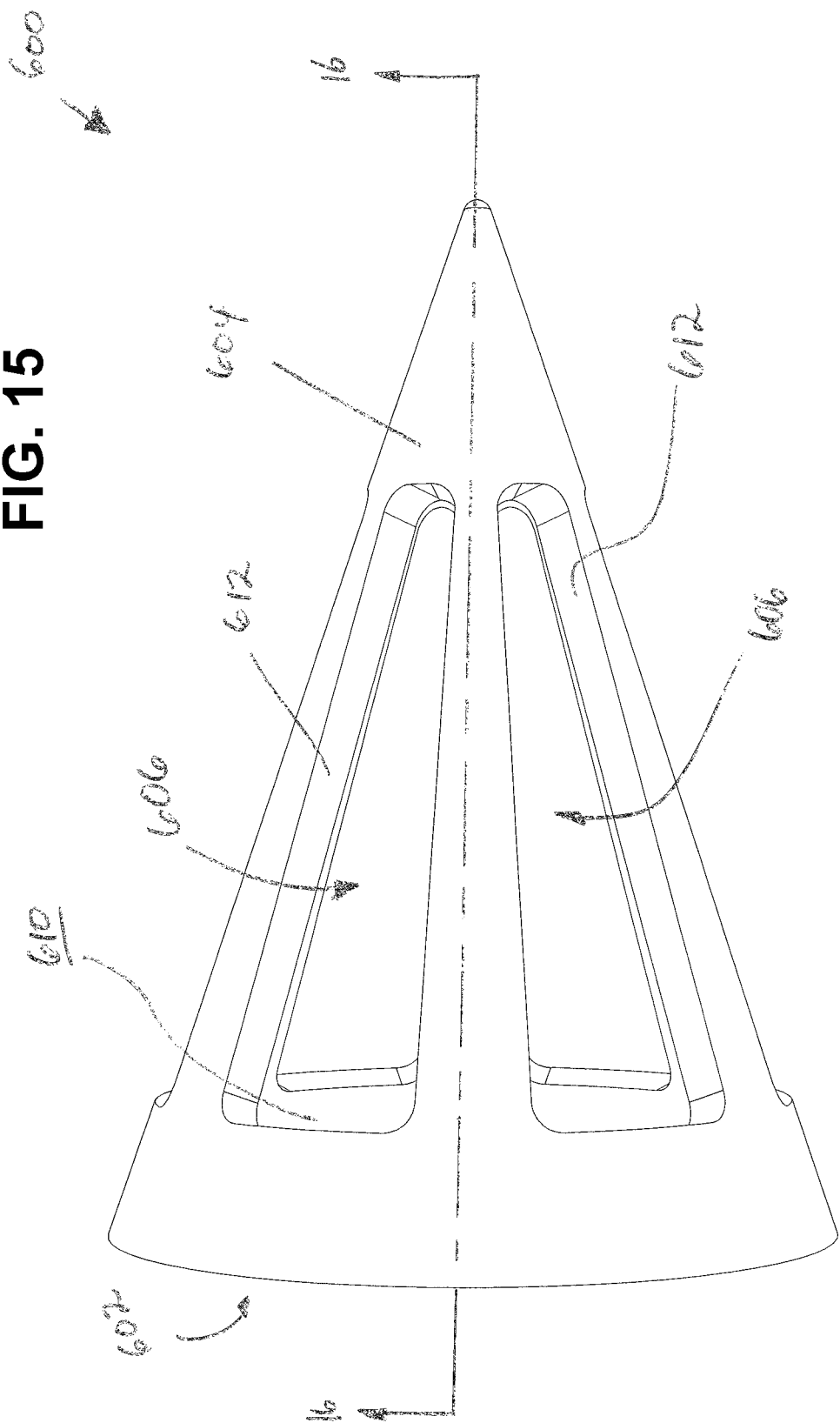
FIG. 15 depicts a side view of the tip of FIG. 14.
Figure 16:
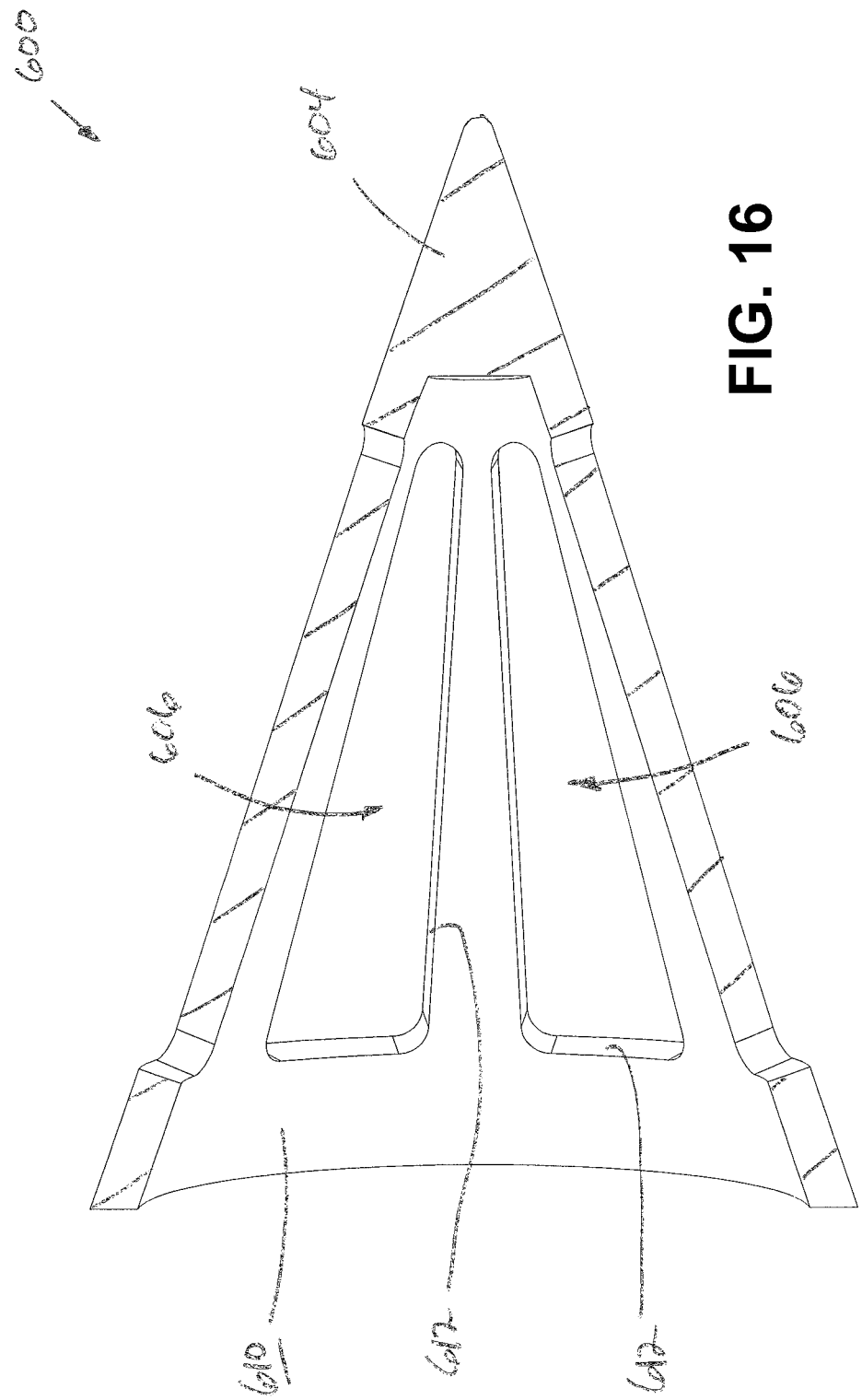
FIG. 16 depicts a cross section view of the tip of FIG. 15, taken along line 16-16 of FIG. 15.
Figure 17:
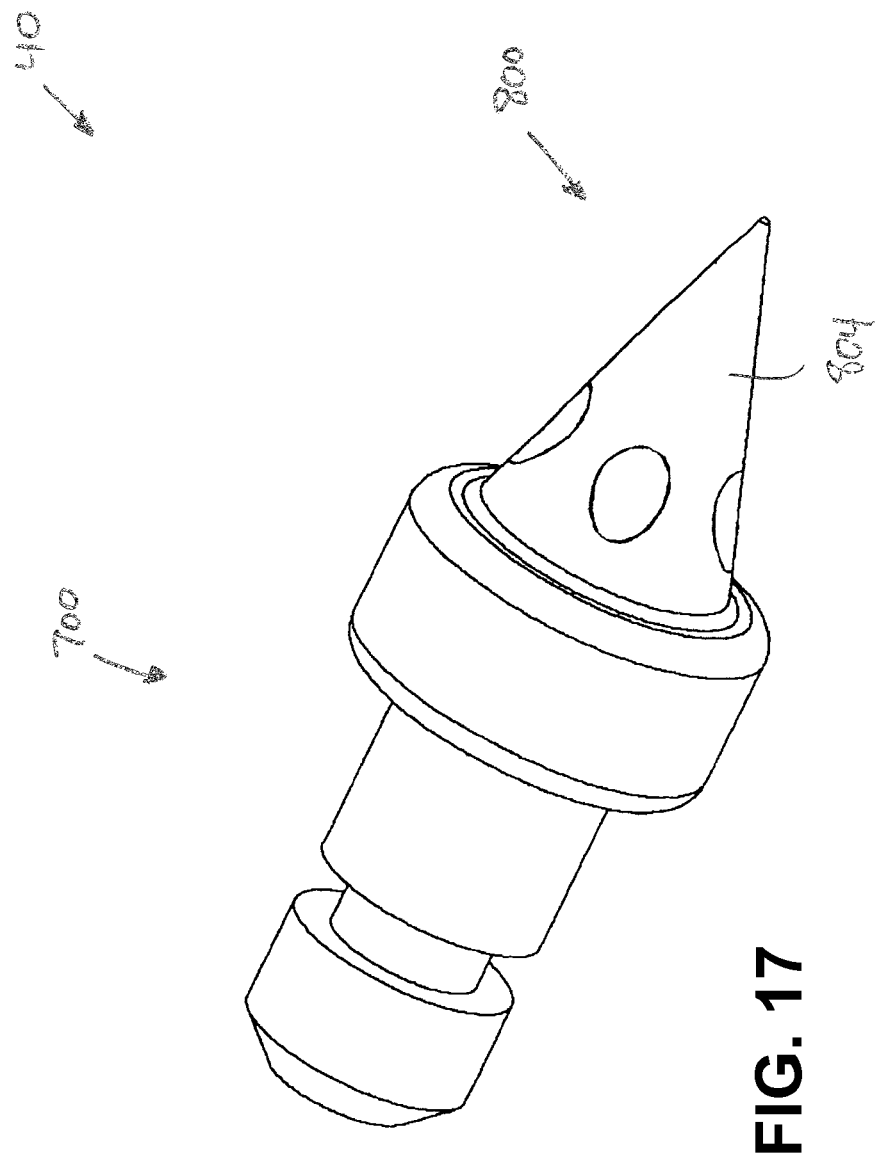
FIG. 17 depicts a perspective view of another exemplary cranial stabilization pin.
Figure 18:
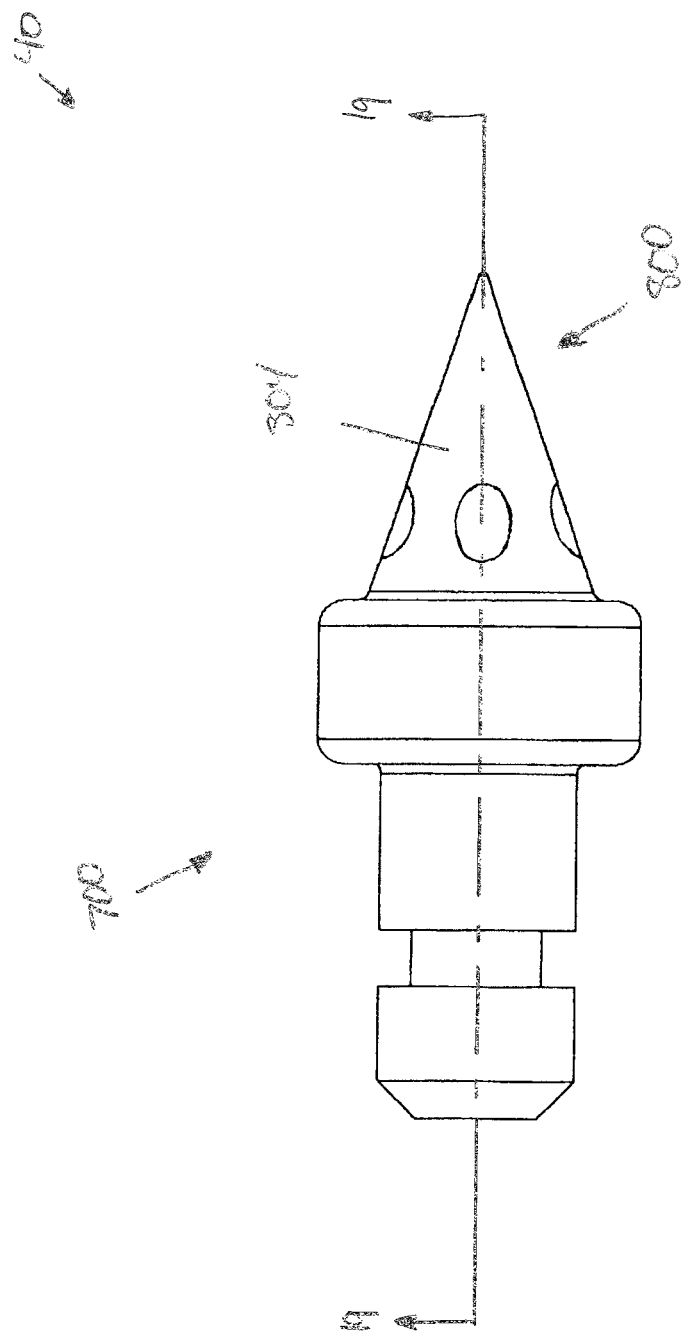
FIG. 18 depicts a side view of the pin of FIG. 17.
Figure 19:
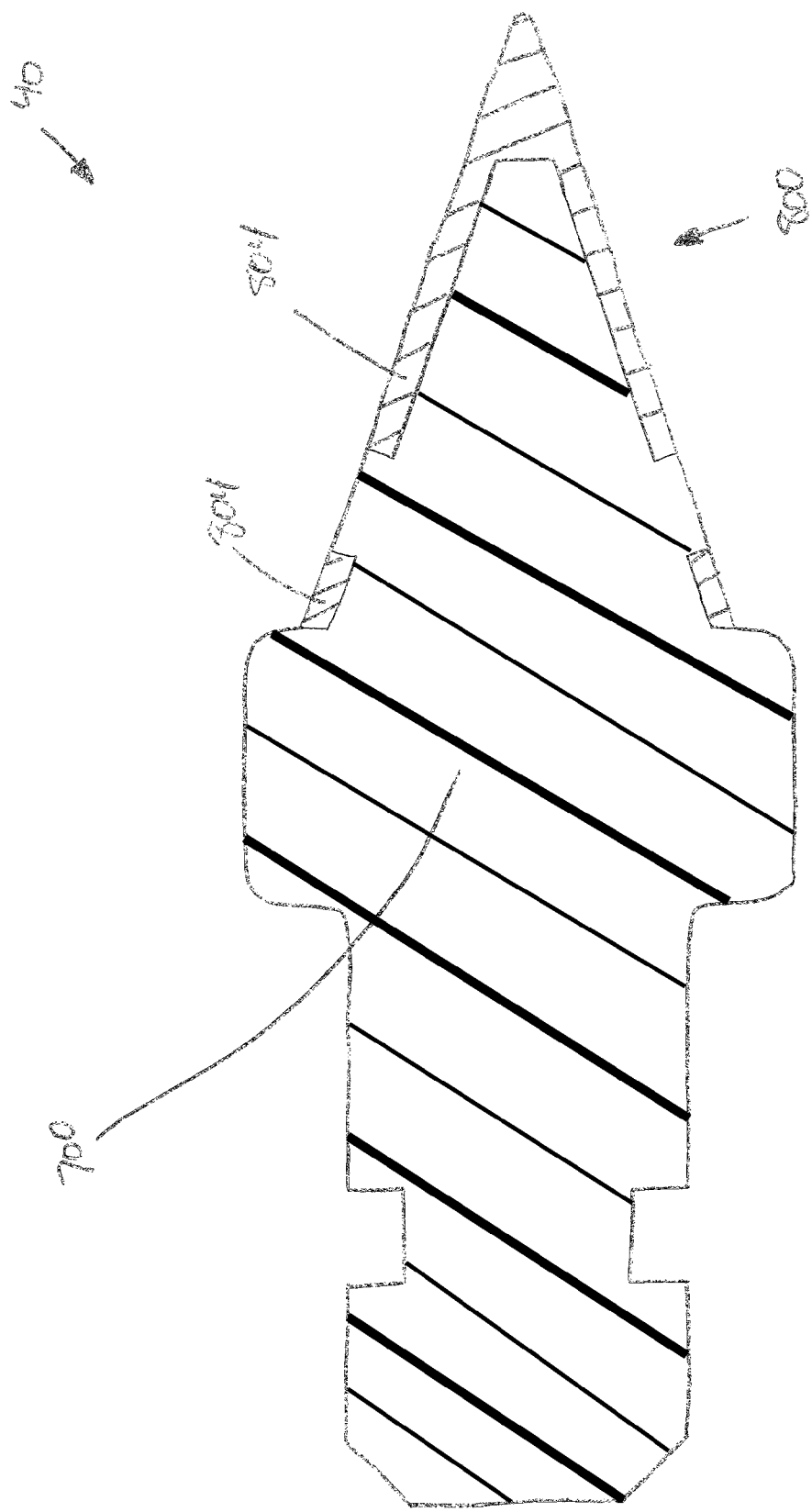
FIG. 19 depicts a cross section view of the pin of FIG. 18, taken along line 19-19 of FIG. 18.
Figure 20:
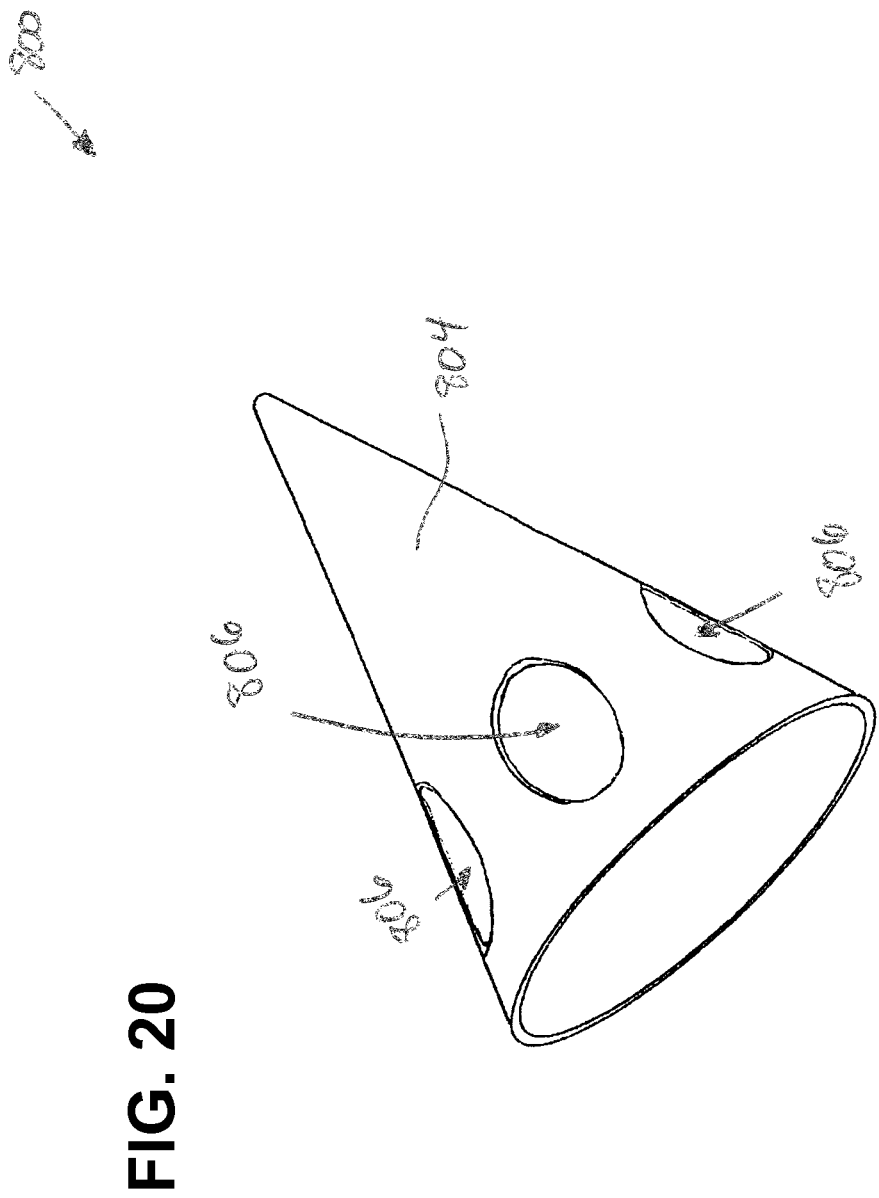
FIG. 20 depicts a perspective view of the tip of the pin of FIG. 17.
Figure 21:
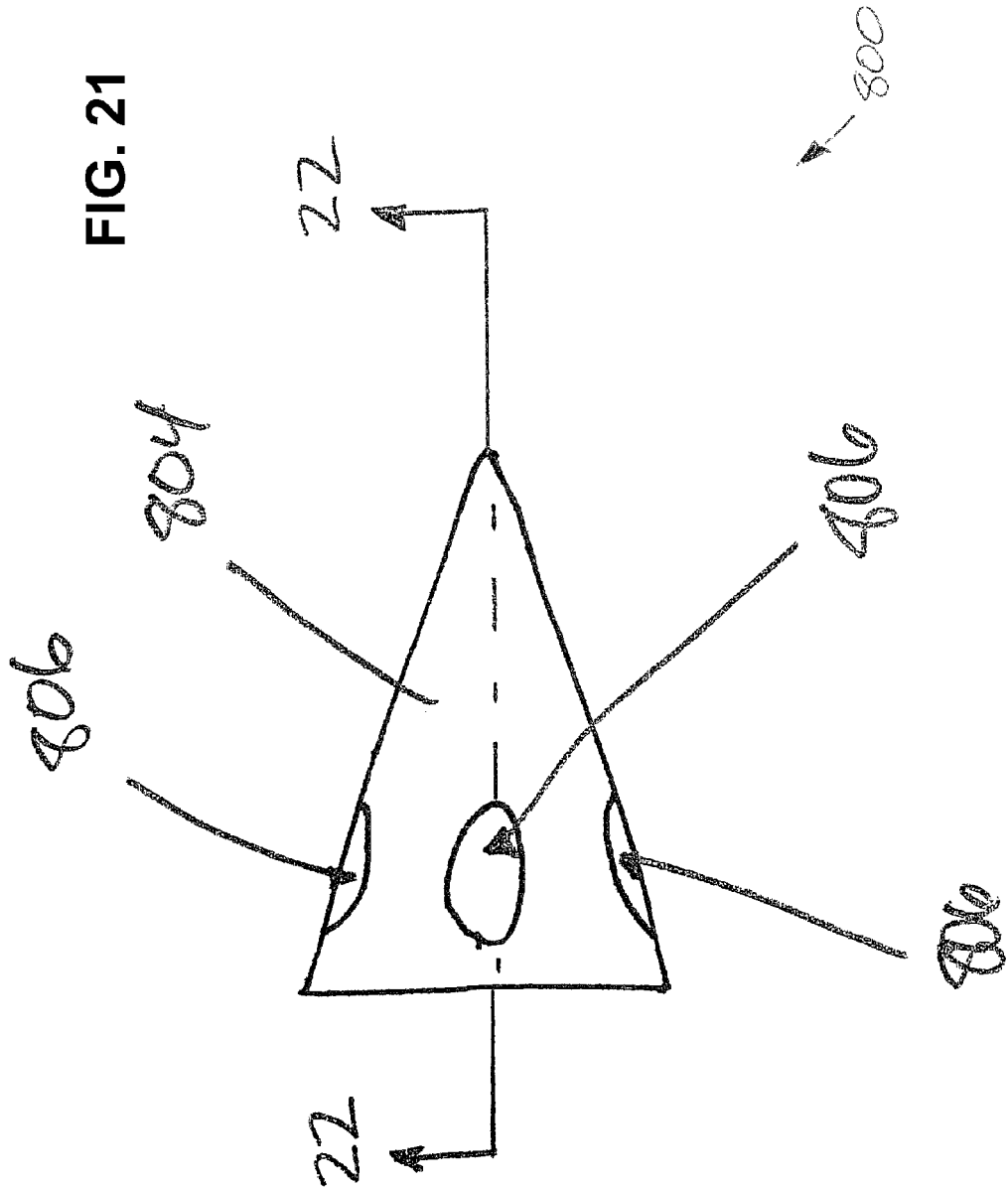
FIG. 21 depicts a side view of the tip of FIG. 20.
Figure 22:
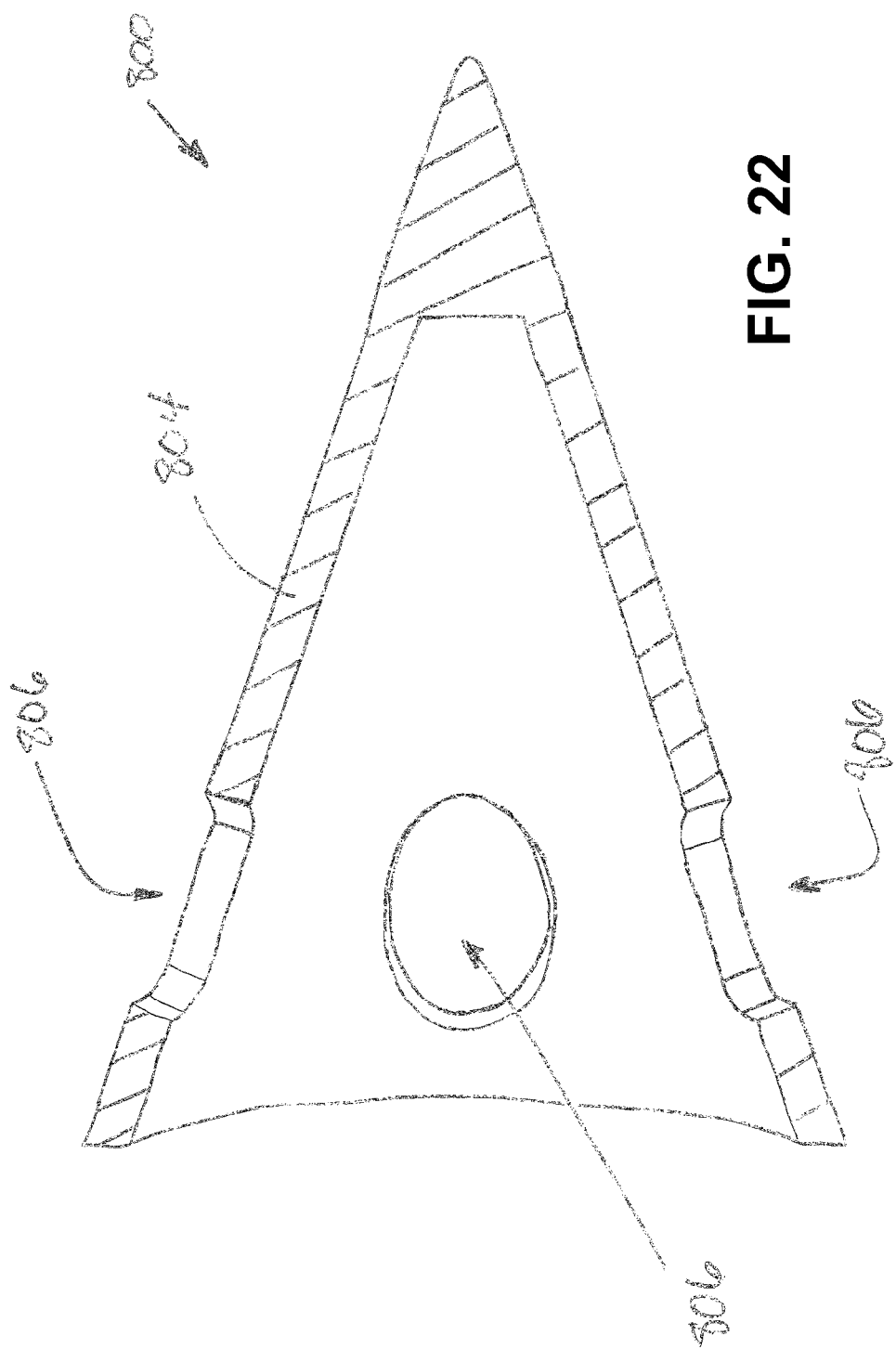
FIG. 22 depicts a cross section view of the tip of FIG. 21, taken along the line 22-22 of FIG. 21.

Referring now to FIGS. 11-16, another exemplary version of a skull pin (30) is shown. Skull pin (30) comprises body (500) and tip (600). Tip (600) is constructed from a non-ferrous, non-magnetic, biocompatible, and suitably strong material. By way of example, and not limitation, a suitable material for tip (600) is titanium. As shown in FIGS. 14-16, tip (600) comprises a cone-shape having inner cavity (602), sidewall (604), and at least one opening (606) in sidewall (604). Sidewall (604) has a thickness that is sufficient to provide the necessary strength during use to avoid failure of pin (30), while limiting the mass of tip (600) such that only minimal artifacts appear in the output of an imaging scan. By way of example only, and not limitation, in some versions the thickness of sidewall (604) is in the range of 0.1 mm to 1 mm. Those of ordinary skill in the art will understand that the thickness of sidewall (604) may be altered in some versions based on the application, imagining technique, and/or other strength influencing factors, e.g. the size and orientation of openings (606) in sidewall (604).

Openings (606) of sidewall (604) provide surface area for bonding tip (600) to body (500) while reducing the mass of tip (600). As mentioned above, the reduction in mass of tip (600) minimizes the appearance of artifacts in the output of imaging scans when pin (30) is used with various imaging technologies. Openings (606) have a triangular shape as shown in FIGS. 14-16. However, other shapes for openings (606) may be suitable as well. For instance, FIGS. 17-22 depict another version of a pin, pin (40), having tip (800) with openings (806) that have an oval shape. Still other shapes for openings (606) may include holes, longitudinal slats, latitudinal slats, diagonal slats, squares, or a combination of shapes. Based on the teachings herein, other suitable shapes for openings (606) will be apparent to those of ordinary skill in the art.

Tip (600) may be manufactured in a variety of ways. For example, fabricating tip (600) may involve metal production processes including casting, forging, flow forming, rolling, extrusion, sintering, metalworking, machining, milling, turning, bending, folding, or combinations of the above. Tip (600) may comprise a single piece or be made from a plurality of pieces securely joined together. In some versions, a single piece of material is folded and the ends of the piece joined together to form tip (600). Where a joining process is used in manufacturing tip (600), the joining processes may include welding, brazing, soldering, or combinations thereof. Still in other versions, a single piece of material is drilled to create inner cavity (602) of tip (600). Tip (600) is then milled and/or turned to create the outer cone or pointed shape. Sidewall (604) of tip (600) is then drilled or cut to create openings (606).

Figure 11:
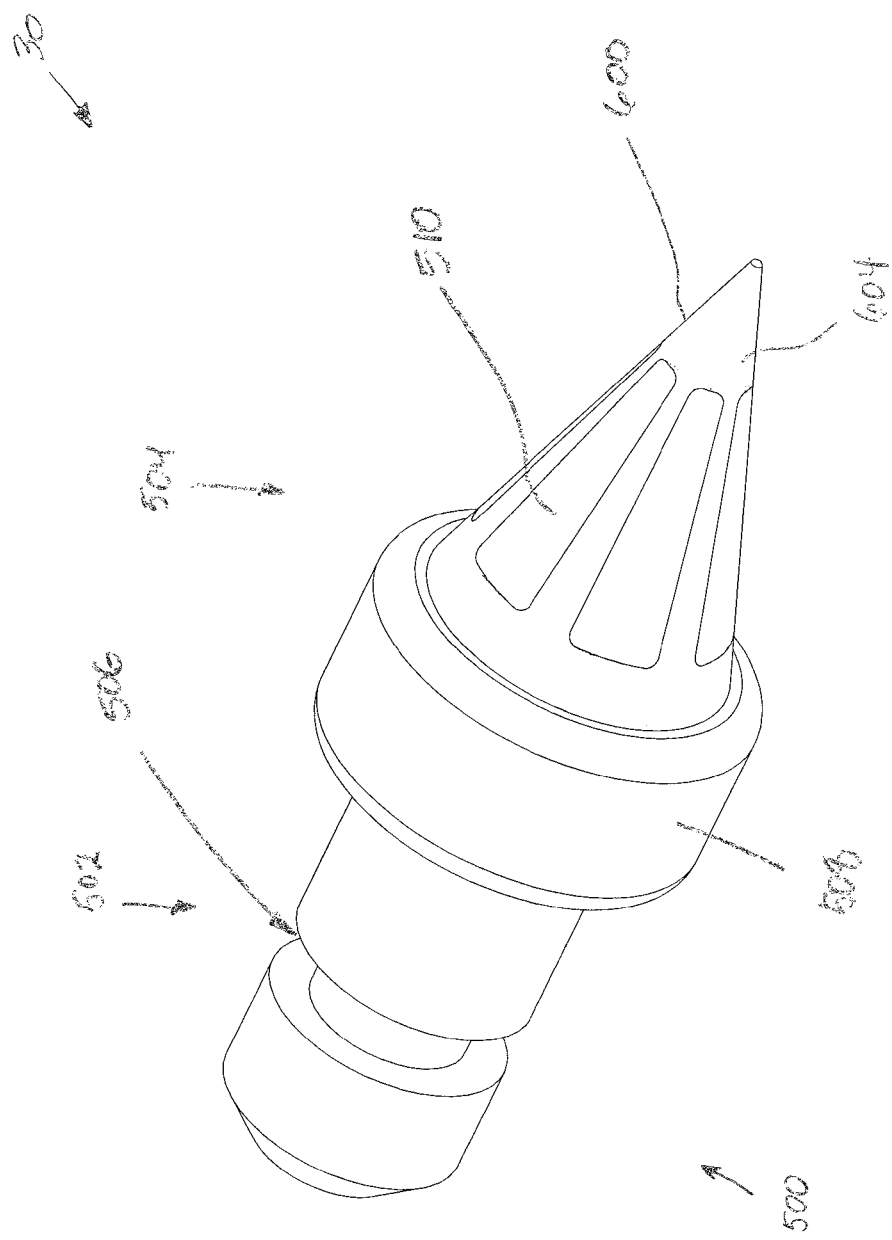
FIG. 11 depicts a perspective view of another exemplary cranial stabilization pin.

FIGS. 11-13 show tip (600) associated with body (500) of pin (30). Body (500) is constructed from a biocompatible radiolucent material that is safe for use with and compatible with MR imaging. Body (500) also has suitable strength and durability for use in a cranial stabilization application. Such a material may be non-ferrous and non-magnetic. Such a material may also be of low density, but with sufficient rigidity and resiliency for use in a cranial stabilization procedure. For instance, in some versions body (500) is comprised of polyether-etherketone (PEEK). Still in other versions, body (500) is comprised of other suitable thermoplastics or thermosetting plastics, which may include glass-fiber and/or carbon-fiber reinforcement. Still yet in other versions body (500) is comprised of duroplastic. Of course other suitable biocompatible radiolucent materials that are safe for use with and compatible with MR imaging may be used for body (500) of pin (30) and will be apparent to those of ordinary skill in the art in view of the teachings herein.

Body (500) comprises proximal end (502) and distal end (504). Distal end (504) is associated with tip (600) of pin (30). Proximal end (502) is associated with other cranial stabilization components. Body (500) is generally comparable to body (100) and body (300) described above. For example, body (500) incorporates annular recess (506), annular collar (508), and first surface (512) of annular collar (508) as described above with reference to body (100) and body (300). A difference between body (500) and the bodies (100, 300) described previously is that conical protrusion (510) of body (500) takes on a different shape to securely fit with tip (600) as will be described further below.

Referring now to the association of tip (600) to body (500), in some versions, body (500) and tip (600) are associated using an injection molding process. In some such versions, body (500) is formed entirely by injection molding while tip (600) is an insert to the injection mold. When molding occurs, the molded material bonds to tip (600) to produce a unitary structure. During the injection molding process, the molten material, e.g. plastic, fills inner cavity (602) of tip (600), bonding with interior surface (610) of inner cavity (602) as well as with the surface areas provided by edges (612) of openings (606) in sidewall (604) of tip (600). In such versions, sidewall (604) of tip (600) remains exposed.

In some versions, tip (600) may incorporate other features, alternatively or in addition to openings (606), to enhance bonding of tip (600) to body (500). For example, interior surface (610) of tip (600) may be configured with grooves or threads to increase the bonded surface area between body (500) and tip (600). Still in other versions, the injection molding material may encapsulate tip (600) so the final appearance of pin (30) is a single injection molded piece, although pin (30) comprises dual components of tip (600) and body (500). In such versions, the injection molding material will also bond with the outer surface, or sidewall (604), of tip (600), thereby increasing the bonded surface area. Based on the teachings herein, other techniques and features to incorporate to produce a pin having a tip that can withstand the torque and axial forces typical with a cranial stabilization procedure while having a low mass tip such that artifacts are minimal in imaging scan outputs will be apparent to those of ordinary skill in the art.

As mentioned above, another exemplary version for a skull pin, pin (40), is shown in FIGS. 17-22. Pin (40) may comprise body (700) and tip (800). The foregoing description regarding FIGS. 11-16 and pin (30) also describe pin (40), with the difference being that the shape of openings (806) in sidewall (804) of tip (800) are oval instead of triangular as with tip (600). Therefore, it shall be understood that the above description regarding pin (30) applies equally to pin (40) with the noted exception regarding the tip opening shape.

Figure 23:
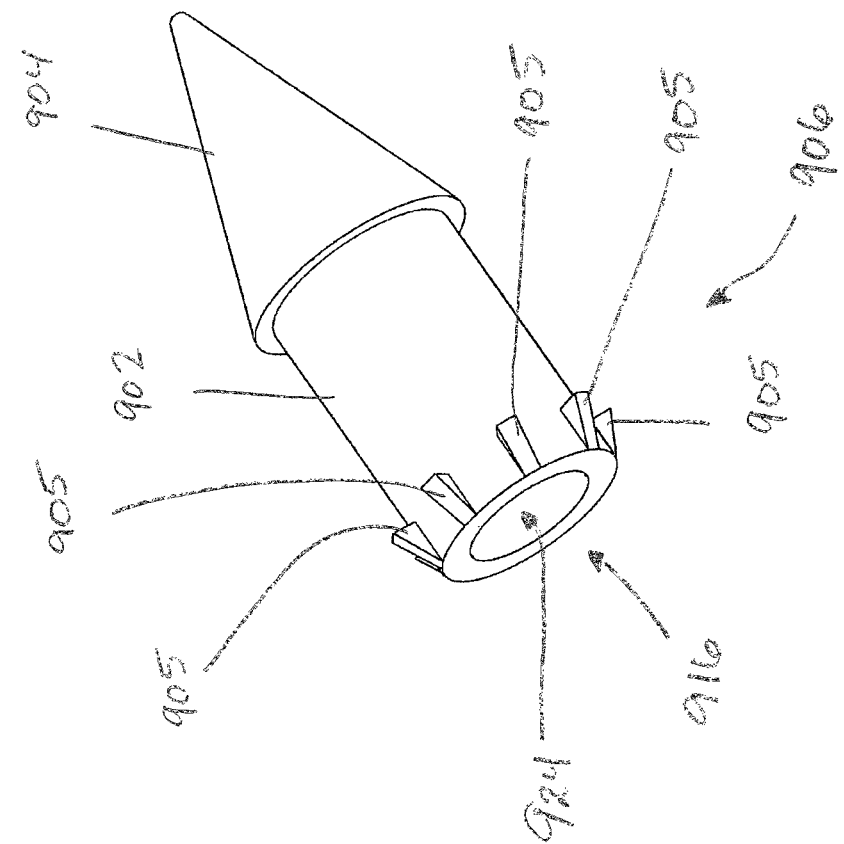
FIG. 23 depicts a perspective view of another exemplary tip for use in a cranial stabilization pin.

Referring now to FIG. 23, another exemplary tip (900) is shown. Tip (900) is configured for use with a body as described previously. Tip (900) comprises shaft (902), conical protrusion (904), and barb anchors (905). In the present example, shaft (902) comprises opening (916) at proximal end (906). Opening (916) provides access to void space (924) within shaft (902). In some versions void space (924) extends through shaft (902) and within conical protrusion (904). As shown in FIG. 23, shaft (902) comprises barb anchors (905) around proximal end (906). Barb anchors (905) provide additional surface area for bonding tip (900) to an exemplary body similar to those described previously. Barb anchors (900) provide a secure connection of tip (900) to a body such that the resultant pin is suitable to withstand the torque and axial forces common in a cranial stabilization procedure.

Figure 24:
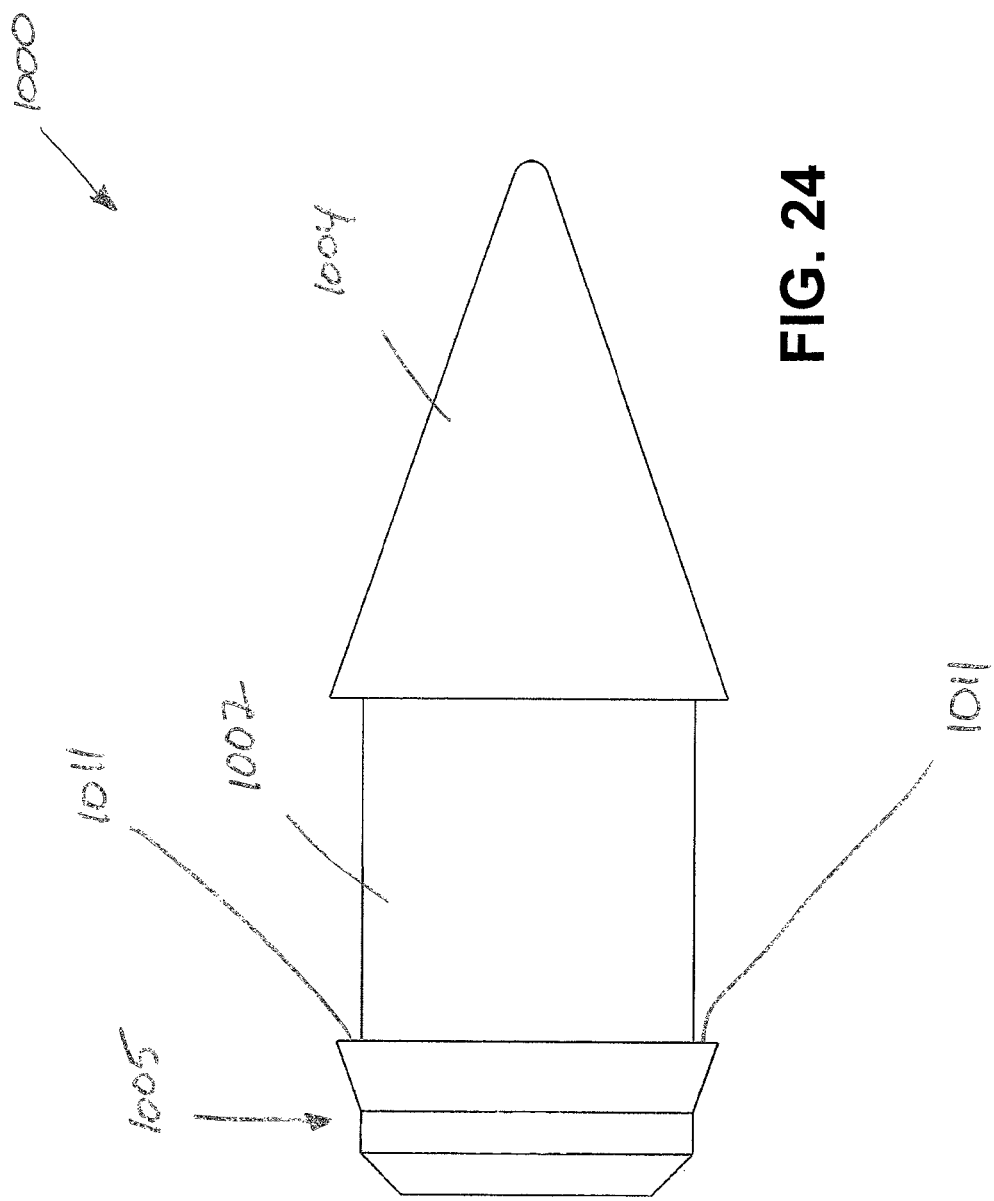
FIG. 24 depicts a side view of another exemplary tip for use in a cranial stabilization pin.

Referring now to FIG. 24, another exemplary tip (1000) is shown. Tip (1000) is configured for use with a body as described previously. Tip (1000) comprises conical protrusion (1004), shaft (1002), and collar (1005). In the present example, tip (1000) is substantially hollow to reduce its mass to reduce artifacts in imaging scans as discussed previously. Of course tip may be substantially or completely solid in other examples. Collar (1005) comprises lip (1011) that extends around the perimeter of collar (1005) and has a larger diameter than shaft (1002) such that lip (1011) overhangs shaft (1002). Lip (1011) provides additional surface area for bonding tip (1000) to a body. Lip (1011) provides a secure connection of tip (1000) to a body such that the resultant pin is suitable to withstand the torque and axial forces common in a cranial stabilization procedure.

Figure 25:
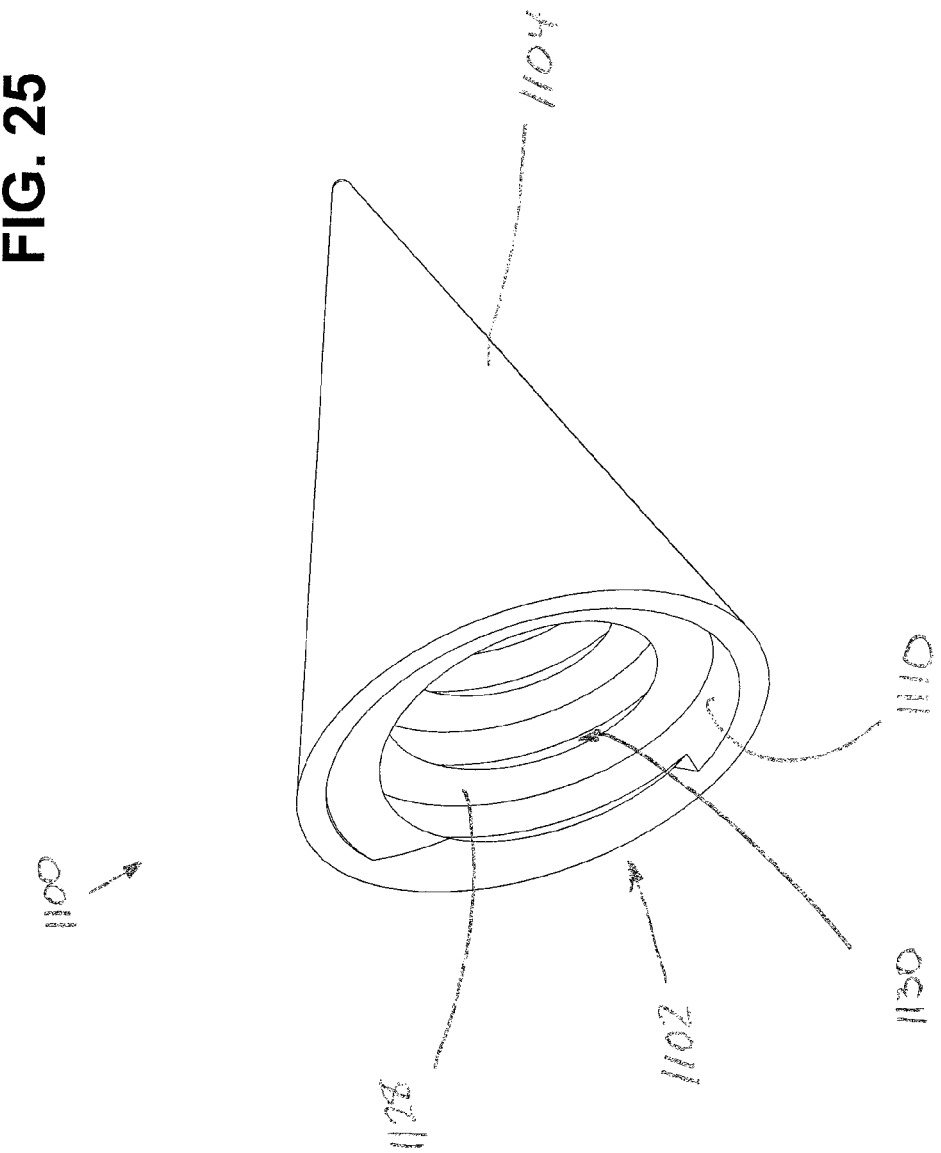
FIG. 25 depicts a perspective view of another exemplary tip for use in a cranial stabilization pin.
Figure 26:
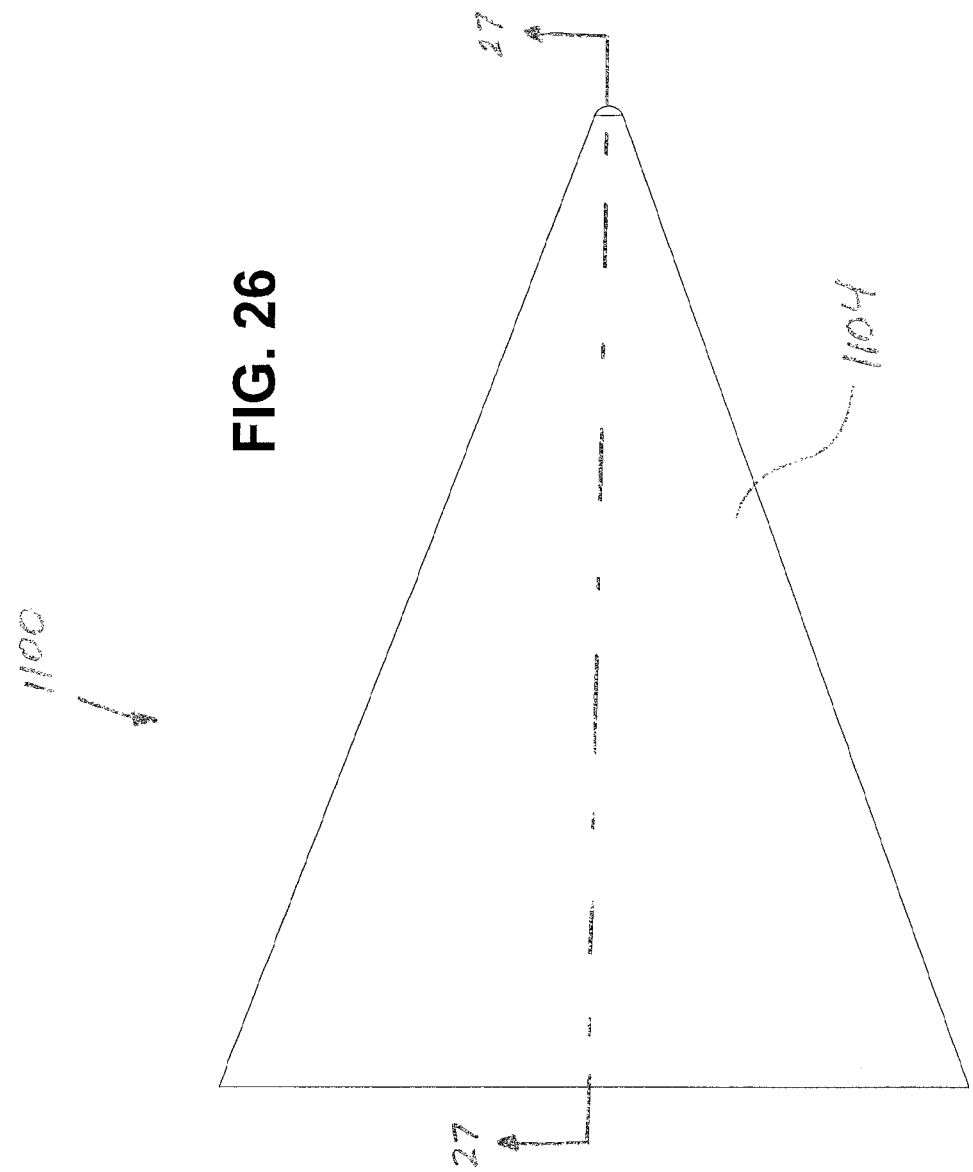
FIG. 26 depicts a side view of the tip of FIG. 25.
Figure 27:
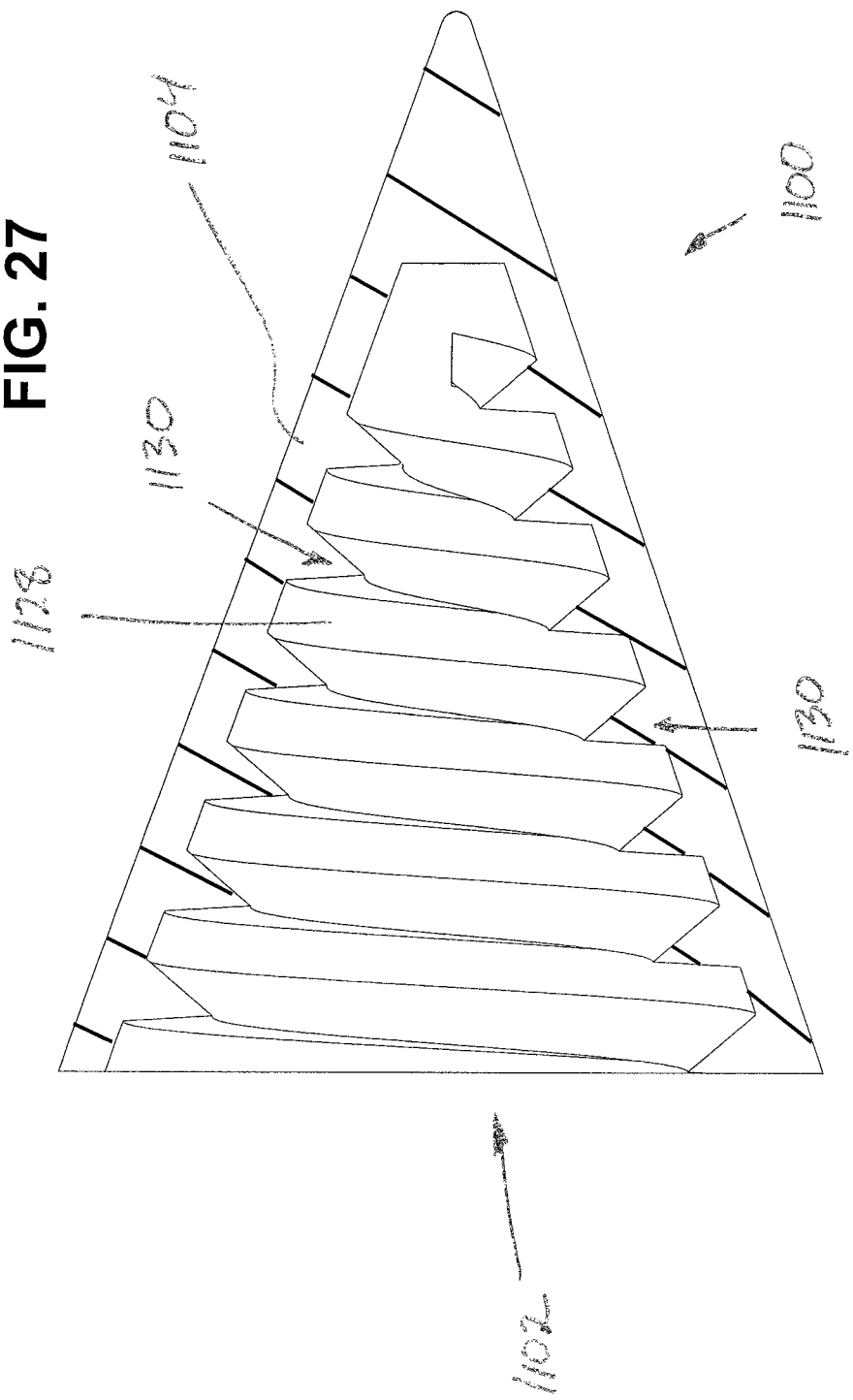
FIG. 27 depicts a cross section view of the tip of FIG. 25, taken along the line 27-27 of FIG. 26.

Referring now to FIGS. 25-27, another exemplary tip (1100) is shown. Tip (1100) comprises inner cavity (1102), sidewall (1104), and interior surface (1110). As shown, sidewall (1104) does not include openings similar to tips (600, 800), of course such openings may be added. Interior surface (1110) of tip (1100) comprises ridges (1128) that extend from one end of tip (1100) to the other end. Ridges (1128) further define gaps (1130). As shown in the present example depicted in FIGS. 25 and 27, ridge (1128) is a continuous spiral-shaped member extending along the interior of tip (1100). Of course multiple discontinuous ridges (1128) with other orientations may be used in other versions, e.g. multiple ridges extending longitudinally within tip (1100) from the open end to the pointed end. Furthermore, based on the teachings herein, those of ordinary skill in the art will understand that other protruding shapes or recesses may be used within the interior of tip (1100) instead of, or in addition to, ridges (1128). In the present example, tip (1100) is secured to a body, e.g. similar to body (500) or body (700), by injection molding, of course other methods of securing tip (1100) to a body may be used, e.g. chemically bonding with an adhesive or mechanical fastening. With injection molding, ridges (1128) provide increased surface area within the interior of tip (1100) for bonding between the body and tip (1100). With such a design, tip (1100) has a sufficient low mass to produce only a minimal artifact in the output of an imaging scan while also having the integrity to withstand the torque and axial forces typical in a skull stabilization procedure. The materials of construction and method of making tip (1100) and the body may be the same or similar to those described for other exemplary pins.

Figure 28:
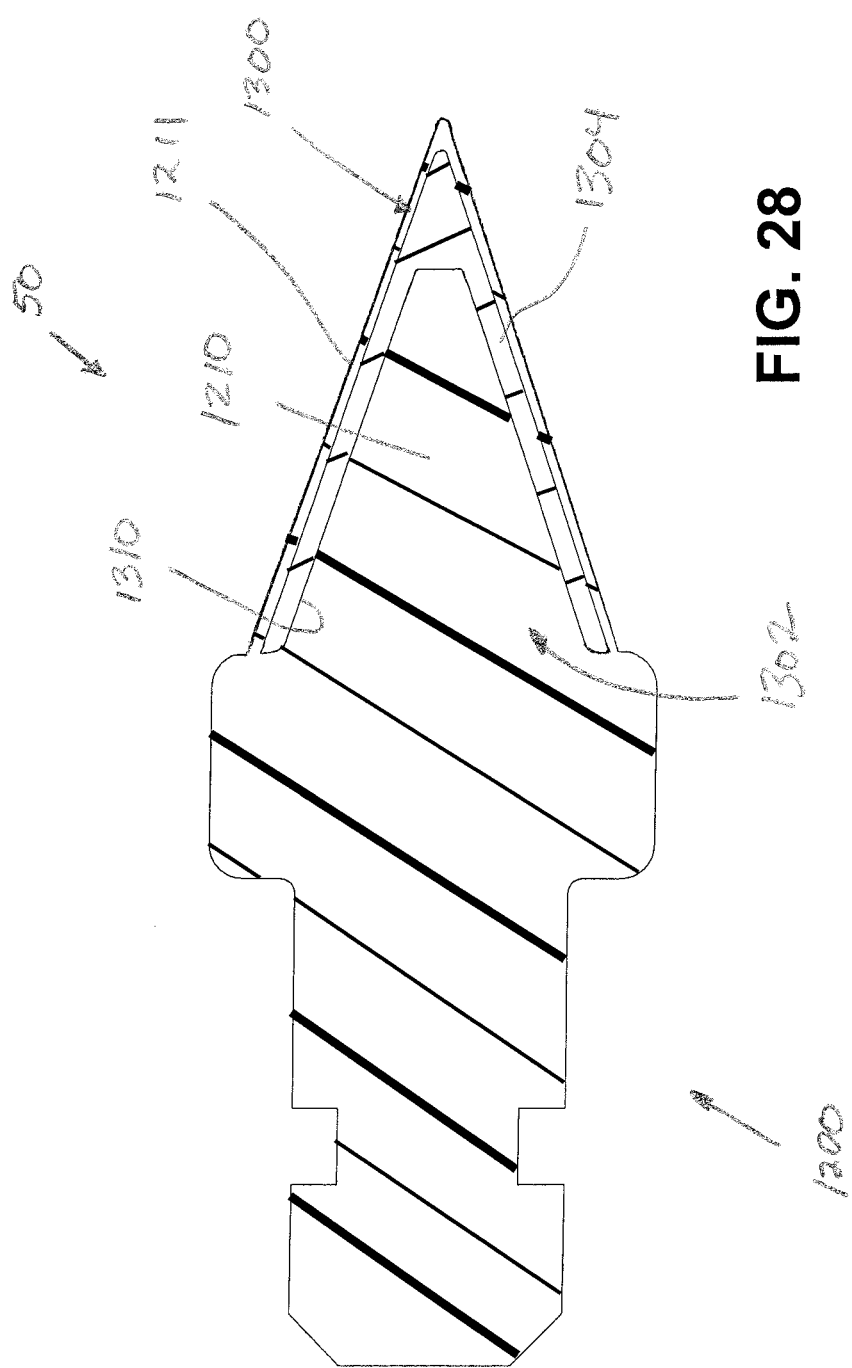
FIG. 28 depicts a cross section view of another exemplary cranial stabilization pin with the tip encased within the body.

Referring now to FIG. 28, another exemplary cranial stabilization pin (50) is shown that incorporates an encased tip. In the present example, pin (50) comprises body (1200) and tip (1300). Tip (1300) is overmolded by body (1200) such that all or substantially all of tip (1300) is surrounded by body (1200). Of course less than substantially all of tip (1300) may be overmolded in some versions such that a distal portion of tip (1300) is visible. In the present example, tip (1300) is similar to the tip shown in FIG. 26, although without internal ridges. Of course, tip (1300) could also be identical to tip (1100) of FIGS. 25-27 in other examples. Furthermore, any of the tips described herein could be adapted for use in a design overmolding the tip with the body. As shown in FIG. 28, tip (1300) comprises interior surface (1310) and internal cavity (1302) that is filled by inner conical protrusion (1210) of body (1200). Sidewall (1304) of tip is surrounded by outer conical sheath (1211) of body (1200) such that tip (1300) is encased within body (1200). In the present example, tip (1300) and body (1200) are secured together by injection molding, where both interior surface (1310) and sidewall (1304) of tip (1300) provide surface area for bonding with conical protrusion (1210) and outer conical sheath (1211) of body (1200). Of course other methods of securing tip (1300) to body (1200) may be used, e.g. chemically bonding with an adhesive or mechanical fastening. In use, tip (1300) of pin (50) has a sufficient low mass to produce only a minimal artifact in the output of an imaging scan while pin (50) also has the integrity to withstand the torque and axial forces typical in a skull stabilization procedure. The materials of construction and method of making pin (50) may be the same or similar to those described for other exemplary pins.

Figure 29:
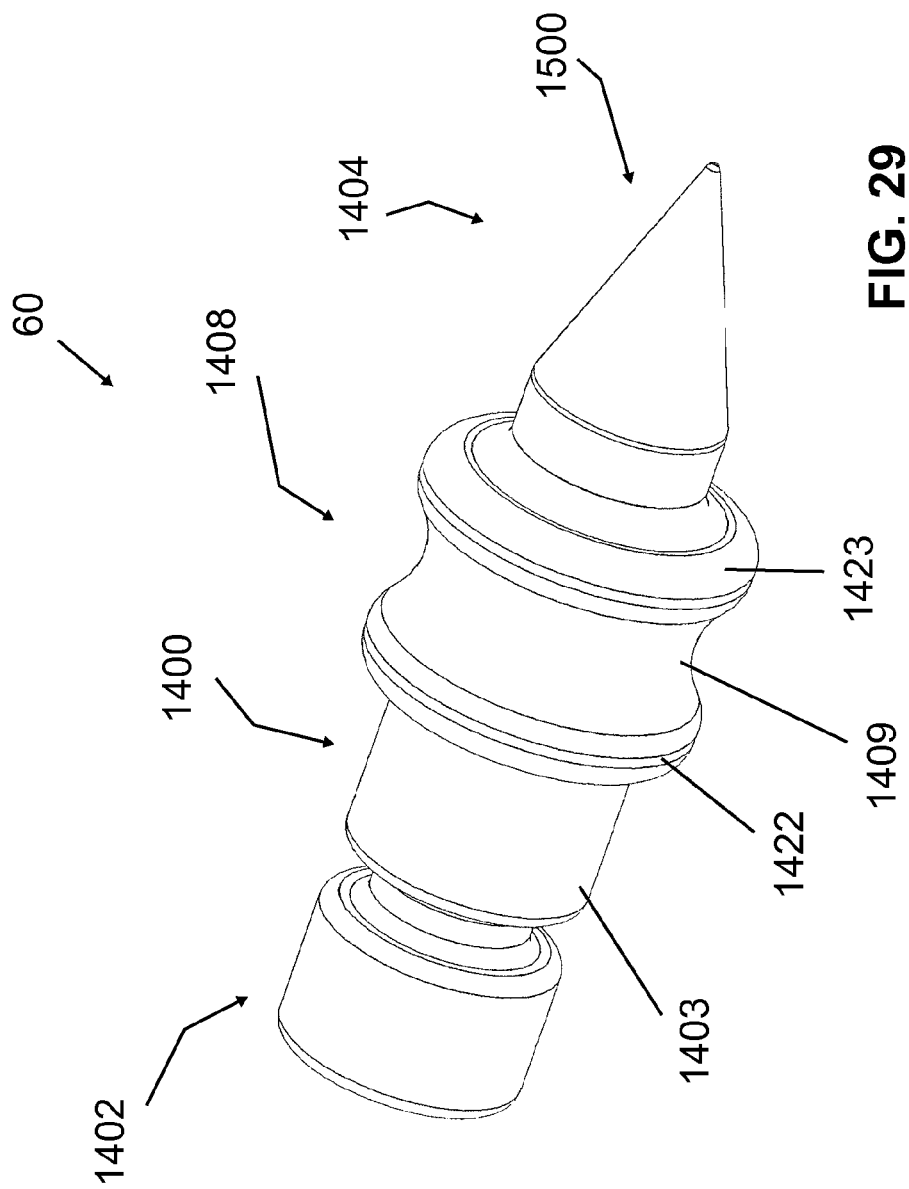
FIG. 29 depicts a perspective view of another exemplary stabilization pin.
Figure 30:
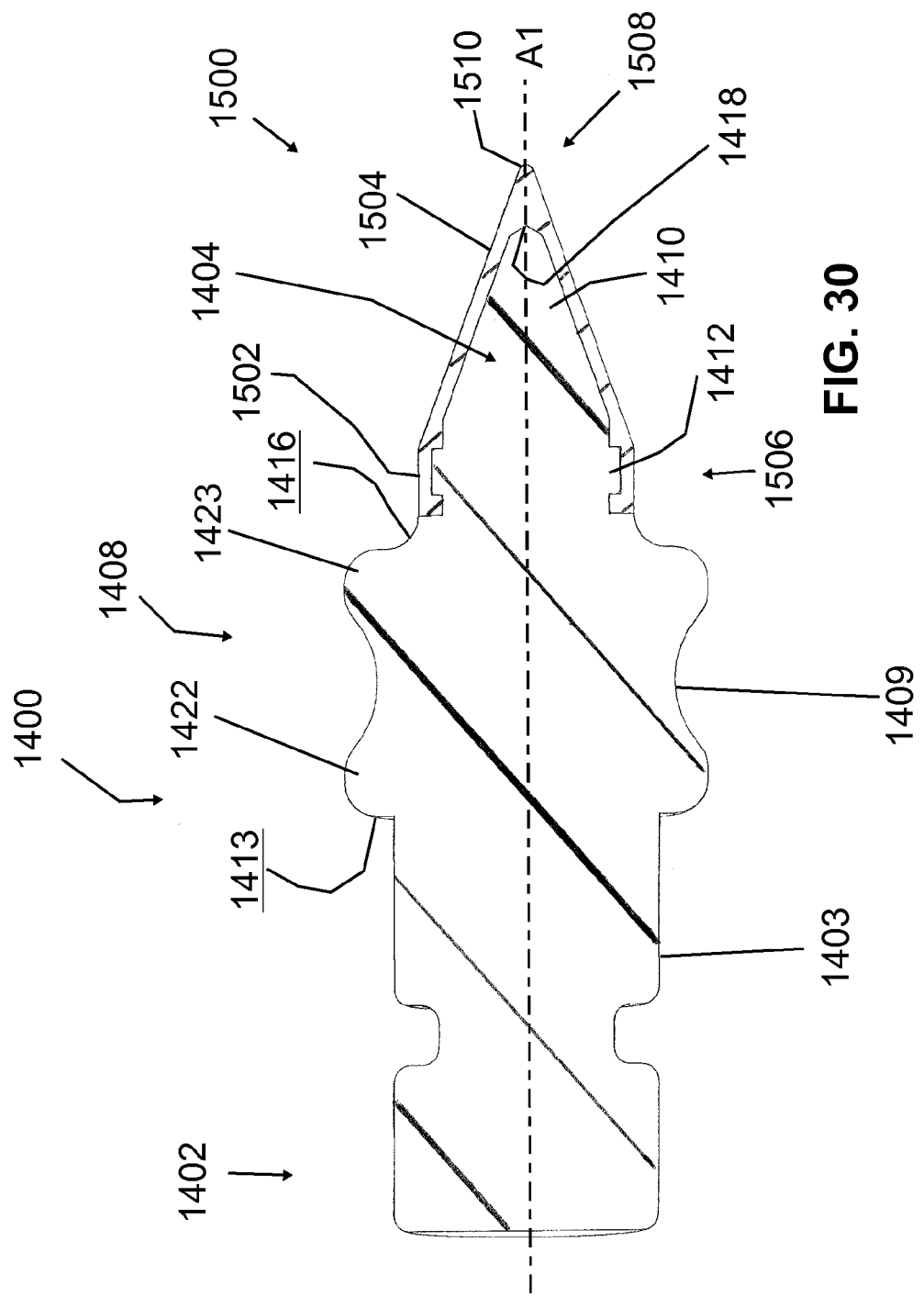
FIG. 30 depicts a cross-sectional side view of the pin of FIG. 29.
Figure 31:
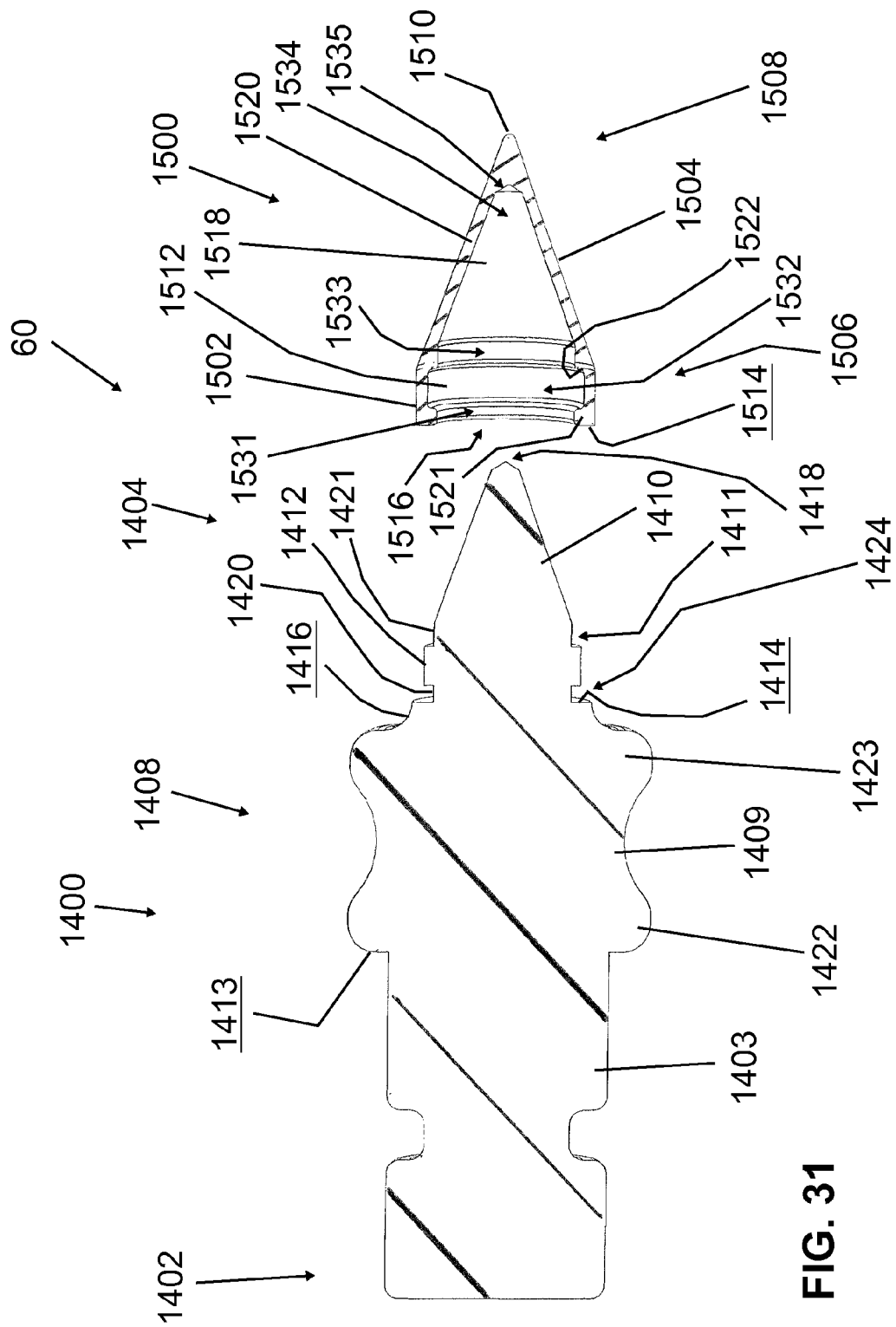
FIG. 31 depicts an exploded cross-sectional side view of the pin of FIG. 29.

FIGS. 29-31 depict various views of an exemplary pin (60), and components thereof, configured for use in a stabilizing device. In some versions pin (60) is used in a head fixation device. Pins (60) are sometimes referred to as skull pins, cranial stabilization pins, stabilization pins, or just pins. Pins (60) are configured to be biocompatible and safe for use with and compatible with imaging techniques including X-ray, computed tomography (CT), and magnetic resonance (MR). Pins (60) are configured as at least partially or substantially radiolucent and are configured to produce only a minimal or limited artifact in the output of an imaging scan. Pins (60) are constructed such that they can withstand the torque and axial forces typical in patient immobilization and in particular in patient head and/or neck stabilization where pins (60) contact a patient's skull.

Referring to FIG. 29, pin (60) comprises body (1400) and a tip (1500). Body (1400) comprises a proximal end (1402) and a distal end (1404), which is at least partly surrounded by tip (1500). Proximal end (1402) is configured for secure attachment with a pin-holding component of a skull clamp or other device, e.g. a skull clamp as described in U.S. Pat. No. 7,836,532, entitled "METHOD AND APPARATUS FOR ATTACHING ACCESSORIES TO A SURGICAL FIXTURE," issued Nov. 23, 2010; U.S. Patent Publication No. 2010/0059064, entitled "METHOD AND APPARATUS FOR USING A SURGICAL FIXTURE IN AN INTRA-OPERATIVE COMPUTED TOMOGRAPHY SCANNER," published Mar. 11, 2010; or U.S. Publication No. 2013/0081636, entitled "HEAD FIXATION DEVICE AND APPARATUS FOR SECURING COMPONENTS THERETO," published Apr. 4, 2013 the disclosures of which are incorporated by reference herein. By way of example, proximal end (1402) has a cylindrical portion (1403) that is configured to fit within a matching bore of a pin-holding component of a skull clamp. Other suitable features and configurations that may be provided at proximal end (1402) such that pin (60) can be associated with a pin-holding component of a skull clamp or other device will be apparent to those of ordinary skill in the art in view of the teachings herein.

Referring now also to FIGS. 30 and 31, distal end (1404) of body (1400) comprises conical portion (1410) and cylindrical portion (1411), which has annular projection (1412). Annular projection (1412) extends outwardly from the remaining portions of cylindrical portion (1411) of distal end (1404) of body (1400). In this manner the diameter of annular projection (1412) is larger than that of the remaining portions of cylindrical portion (1411). In particular, first and second portions (1420, 1421) of cylindrical portion (1411) are adjacent to each side of annular projection (1412), and first and second portion (1420, 1421) have a smaller diameter than annular projection (1412). Annular projection (1412) is configured to provide for coupling tip (1500) to body (1400) as discussed in further detail below. Conical portion (1410) extends distally from body (1400), tapering from larger to smaller diameter as conical portion (1410) extends distally. At a distal-most end, conical portion (1410) comes to point (1418). In view of the teachings herein, other types of features and configurations for distal end (1404) of body (1400), or modifications of distal end (1404) of body will be apparent to those of ordinary skill in the art.

Proximal to distal end (1404) is annular collar (1408) that provides ridges (1422, 1423) separated by annular recess (1409). Annular recess (1409) can be a gripping feature for a user's handling of pin (60). At the proximal side of ridge (1422) is first surface (1413) that is configured to act as a stop by contacting a portion of a pin-holding component of a skull clamp or other device. At the distal side of annular collar (1408) is ridge (1423) that comprises radial surface (1416). Radial surface (1416) extends and connects with the distal-most end of annular collar (1408) defined by second surface (1414). With the difference in diameters of the distal-most end of annual collar (1408), first portion (1420) of cylindrical portion (1411), and annular projection (1412), recess (1424) is defined between annular projection (1412) and second surface (1414) of annular collar (1408).

Tip (1500) is largely a hollow structure comprising a cylindrical portion (1502) and a conical portion (1504) both defined by a thin wall (1520) that is shaped to form tip (1500). Wall (1520) comprises an interior surface and an exterior surface. Cylindrical portion (1502) is located along proximal end (1506) of tip (1500), and conical portion (1504) is located along distal end (1508) of tip (1500). Conical portion (1504) extends distally from cylindrical portion (1502), tapering to a point (1510) at its distal-most end. Together cylindrical portion (1502) and conical portion (1504) define a hollow interior (1518) or void space. Stated another way, interior surface of wall (1520) defines hollow interior (1518). Conical portion (1504) is configured to receive conical portion (1410) of body (1400), while cylindrical portion (1502) is configured to receive cylindrical portion (1411) of body (1400). Cylindrical portion (1502)

further defines distal open end (1516) that leads to hollow interior (1518) or void space. An interior surface of cylindrical portion (1502) provides an annular recess (1512) that is configured to receive annular projection (1412) of cylindrical portion (1411) of body (1400) when pin (10) is formed or assembled.

Annular recess (1512) is defined partially by proximal and distal protrusions or projections (1521, 1522) that extend from wall (1520) inward toward a longitudinal axis (A1) of pin (60). With this configuration, hollow interior (1518) comprises a shape having three connected cylindrical void spaces (1531, 1532, 1533), with the combined three connected void spaces further connecting with a conical void space (1534). In the present example, the distal-most end of hollow interior (1518) provides for a second conical void space (1535) that terminates in a point, where this second conical void space (1535) is connected with the larger conical void space (1534). Collectively void spaces (1531, 1532, 1533, 1534, 1535) define hollow interior (1518). In other versions, void space (1535) can be omitted. Other modifications to the shape of hollow interior (1518) will be apparent to those of ordinary skill in the art in view of the teachings herein.

In the present example, tip (1500) is constructed from a non-magnetic metal, such as titanium. During fabrication, a solid piece of titanium is processed to create the general shape as shown in the illustrated version. The shaped titanium piece can be machined using various steps and processes, e.g. tip (1500) can be drilled along longitudinal axis (A1) in some versions using various drilling bits and sequences to hollow-out tip (1500) and create open end (1516) and hollow interior (1518). Based on the teachings herein, other ways to fabricate tip (1500) and other materials suitable for tip (1500) will be apparent to those of ordinary skill in the art. By way of example only, other suitable materials to fabricate the tips disclosed herein may include ceramics, other non-magnetic metals, glass-fiber reinforced materials, carbon-fiber reinforced materials, and sapphire, among others.

In some versions, body (1400) is constructed from a plastic. Suitable plastics may include polyether ether ketone (PEEK), duroplastic, and/or other thermoplastics or thermosetting plastics, all or any of which may include glass-fiber and/or carbon-fiber reinforcement. In the present example, tip (1500) is connected with body (1400), and body (1400) is formed, during an injection molding process. In this example, a mold containing tip (1500) is filled with a polymeric material. During this process the fluid or molten polymeric material flows into hollow interior (1518) of tip. Once the polymeric material hardens, it bonds to tip (1500) to thereby securely fasten tip (1500) with body (1400). In this way, a process is used to make pin (60) where body (1400) is formed at the same time as tip (1500) is bonded or attached with body (1400). With this process, annular recess (1512) of tip (1500) is filled with polymeric material of body (1400) that becomes or is formed into annular projection (1412). Similarly recess (1424) of body (1400) is formed and receives protrusion (1521) of tip (1500). Also, in the present example, with the exception of bonding that occurs between surfaces (1414) of body (1400) and surface (1514) of tip (1500), all of the bonding between body (1400) and tip (1500) occurs along the interior surfaces of tip (1500) that defines hollow interior (1518).

In some versions, for example the illustrated version, tip (1500) can be exposed in the finished pin (60). In some other versions, the polymeric material can be molded within and over tip (1500) such that some or all of tip (1500) is not exposed in the finished pin (60). In some versions of pin (60), body (1400) could be separately molded and then tip (1500) may be snap-fit to body (1400) such that annular recess (1512) receives annular projection (1412) of body (1400), and recess (1424) of body (1400) receives protrusion (1521) of tip (1500) such that tip (1500) is securely attached to body (1500) to form assembled pin (60).

Referring to FIGS. 30 and 31, when pin (60) is fully formed and assembled, surface (1514) of cylindrical portion (1502) of tip (1500) abuts second surface (1414) of body (1400). Similarly, the surface of conical portion (1410) of body (1400) abuts the interior of wall (1520) within hollow interior (1518) in conical portion (1504) of tip (1500). Furthermore, there are other abutments between surfaces, e.g., where annular projection (1412) of body (1400) is received within annular recess (1512) of tip (1500). In particular, the abutment between the sides of annular projection (1412) of body (1400) and protrusions (1521, 1522) of tip (1500). While the primary restriction of movement of tip (1500) relative to body (1400) is provided by the surface bonding that occurs between tip (1500) and body (1400) during injection molding, the present example does provide at least two abutting surfaces between body (1400) and tip (1500) that would further prevent or inhibit movement of tip (1500) in the proximal or distal directions along longitudinal axis (A1).

The transition of tip (1500) to body (1400) of pin (60) is provided as a smooth transition. In the present example, this is achieved by having a diameter of exterior surface of cylindrical portion (1502) that is substantially similar to a minimal diameter of annular collar (1508) along radial surface (1416). In the present example, this transition between tip (1500) and body (1400) is generally configured such that the transition is parallel with the longitudinal axis (A1) of pin (60).

The configuration, design, and fabrication of pin (60) shown and described above, results in pin (60) being biocompatible, safe for use with, and compatible with MR imaging. Furthermore, as mentioned, pin (60) is substantially radiolucent with a strong tip (1500) having low mass (contributed to by its hollow design and thin wall) such that only a minimal or limited artifact, if any, is seen in the output of an imaging scan. Furthermore, using such a design and fabrication process, tip (1500) and body (1400) are securely joined such that pin (60) can withstand the torque and axial forces typical in a stabilization procedure using a skull clamp or other device. For instance, molding body (1400) to tip (1500) by molding plastic within hollow interior (1518) of tip (1500) where there are two or more abutting surfaces between tip (1500) and body (1400) within hollow interior (1518) of tip (1500) provides a strong and secure connection between body (1400) and tip (1500), suitable for withstanding torque and axial forces experienced in use.

While above exemplary pins have been described as having a molded body bonded to a tip, other connection methods for securing a tip to a body will be apparent to those of ordinary skill in the art in view of the teachings herein. For example, body could be molded separately from tip and tip may be secured to body with a suitable fastener. In some versions, tip may snap-fit to body. In other versions tip may be screwed to body. Still in some other versions tip may be glued or chemically adhered to body. Also, any of the bodies described may be constructed by machining, e.g. milling, turning, etc., instead of or in addition to molding.

Based on the teachings herein, it will be appreciated by those of ordinary skill in the art that in any of the described examples, and examples not explicitly described but within the scope of the claims, the sizes and proportions of the tip and body may be altered. For example, the tip may be sized such that the portion of the tip extending from the body is small such that the output of an imaging scan shows a minimal artifact. Furthermore, the tip may be sized such that the portion of the tip extending from the body is generally equivalent to the portion of the tip that would penetrate the patient's skull during a stabilization procedure. In such an example, the exposed portion of the tip when not in use would be covered by bone when in use. With such a design, artifacts in the output of imaging scans may be minimized with the tip not exposed when in use.

Having shown and described various versions of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometries, materials, dimensions, ratios, steps, and the like discussed above are illustrative and are not required. Accordingly, the scope of the present invention should be considered in terms of whatever claims recite the invention, and is understood not to be limited to the details of structure and operation shown and described in the description.

What is claimed is:

1. A skull pin for use with a stabilizing device, wherein the pin comprises:
   a. a tip, wherein the tip is configured to contact a patient's skull, wherein the tip comprises:
      i. a conical portion,
      ii. a point at a distal end of the tip, wherein the point is configured to contact the patient's skull,
      iii. a substantially thin sidewall, wherein the substantially thin sidewall comprises an exterior surface and an interior surface,
      iv. a hollow interior, and
      iv. one or more protrusions formed in the interior surface of the sidewall; and
   b. a molded body, wherein the molded body comprises;
      i. a proximal end dimensioned to fit in an opening of a skull clamp arm, and
      ii. a distal end secured to and extending within the hollow interior of the tip and contacting the one or more protrusions, wherein the tip is an insert piece bonded to the molded body during molding to form a unitary structure for the skull pin where the tip is non-removable from the molded body.

2. The pin of claim 1, wherein the one or more protrusions extend toward a longitudinal axis of the pin.

3. The pin of claim 1, wherein the tip further comprises an annular recess.

4. The pin of claim 3, wherein the annular recess defines the one or more protrusions.

5. The pin of claim 3, wherein the molded body comprises an annular projection configured to fit within the annular recess of the tip.

6. The pin of claim 1, wherein the hollow interior of the tip comprises a plurality of void spaces.

7. The pin of claim 6, wherein the plurality of void spaces are connected.

8. The pin of claim 6, wherein one of the plurality of void spaces is a conically shaped.

9. The pin of claim 1, wherein the pin is substantially radiolucent.

10. The pin of claim 1, wherein the tip is comprised of titanium and the body is comprised of plastic.

11. The pin of claim 1, wherein the molded body comprises an annular collar.

12. The pin of claim 11, wherein the annular collar comprises an annular recess.

13. The pin of claim 12, wherein the annular collar further comprises a first ridge and a second ridge, wherein the annular recess is positioned between the first ridge and the second ridge.

14. The pin of claim 1, wherein the tip further comprises a cylindrical portion, and wherein the molded body further comprises a radial surface that aligns with the cylindrical portion of the tip.

* * * * *